(12) United States Patent
Mayer

(10) Patent No.: US 7,790,418 B2
(45) Date of Patent: Sep. 7, 2010

(54) ISOTHERMAL AMPLIFICATION OF NUCLEIC ACIDS ON A SOLID SUPPORT

(75) Inventor: Pascal Mayer, Eloise (FR)

(73) Assignees: Illumina Cambridge Limited, Nr. Saffron Walden (GB); Illumina, Inc., San Diego, CA (US)

( * ) Notice: Subject to any disclaimer, the term of this patent is extended or adjusted under 35 U.S.C. 154(b) by 713 days.

(21) Appl. No.: 10/433,965

(22) PCT Filed: Dec. 7, 2001

(86) PCT No.: PCT/EP01/14369
§ 371 (c)(1), (2), (4) Date: Nov. 3, 2003

(87) PCT Pub. No.: WO02/46456
PCT Pub. Date: Jun. 13, 2002

(65) Prior Publication Data
US 2004/0096853 A1 May 20, 2004

(30) Foreign Application Priority Data
Dec. 8, 2000 (EP) ................................. 00127011

(51) Int. Cl.
*C12P 19/34* (2006.01)
(52) U.S. Cl. ..................................................... 435/91.2
(58) Field of Classification Search ........................ None
See application file for complete search history.

(56) References Cited

U.S. PATENT DOCUMENTS

| | | |
|---|---|---|
| 4,719,179 A | 1/1988 | Barany |
| 5,093,245 A | 3/1992 | Keith et al. |
| 5,326,692 A | 7/1994 | Brinkley et al. |
| 5,455,166 A * | 10/1995 | Walker ................. 435/91.2 |
| 5,508,169 A | 4/1996 | Deugau et al. |
| 5,514,539 A | 5/1996 | Bukh et al. |
| 5,589,332 A | 12/1996 | Shih et al. |
| 5,616,478 A | 4/1997 | Chetverin et al. |
| 5,641,658 A | 6/1997 | Adams et al. |
| 5,645,994 A | 7/1997 | Huang |
| 5,750,337 A | 5/1998 | Squirrell |
| 5,753,439 A | 5/1998 | Smith et al. |
| 5,800,992 A | 9/1998 | Fodor et al. |
| 5,837,466 A | 11/1998 | Lane et al. |
| 5,843,660 A | 12/1998 | Schumm et al. |

(Continued)

FOREIGN PATENT DOCUMENTS

EP 0 224 126 A2 6/1987

(Continued)

OTHER PUBLICATIONS

Lizardi et al., 1998, Nature Genetics, vol. 19, pp. 225-232.*

(Continued)

*Primary Examiner*—Mark Staples
(74) *Attorney, Agent, or Firm*—Klauber & Jackson LLC

(57) ABSTRACT

Methods for isothermal amplification of nucleic acid by the means of a solid support are disclosed. These methods are useful for applications needing high throughput, in particular nucleic acid sequencing.

27 Claims, 10 Drawing Sheets

U.S. PATENT DOCUMENTS

| | | | |
|---|---|---|---|
| 5,939,291 | A | 8/1999 | Loewy et al. |
| 5,942,391 | A * | 8/1999 | Zhang et al. ............... 435/6 |
| 6,033,881 | A * | 3/2000 | Himmler et al. .......... 435/91.2 |
| 6,045,994 | A | 4/2000 | Zabeau et al. |
| 6,054,276 | A | 4/2000 | Macevicz |
| 6,060,288 | A | 5/2000 | Adams et al. |
| 6,090,592 | A | 7/2000 | Adams et al. |
| 6,107,023 | A | 8/2000 | Reyes et al. |
| 6,114,149 | A | 9/2000 | Fry et al. |
| 6,277,606 | B1 | 8/2001 | Wigler et al. |
| 6,300,070 | B1 * | 10/2001 | Boles et al. ............... 435/6 |
| 6,361,947 | B1 | 3/2002 | Dong et al. |
| 6,406,893 | B1 | 6/2002 | Knapp et al. |
| 6,468,751 | B1 | 10/2002 | Adams et al. |
| 7,115,400 | B1 | 10/2006 | Adessi et al. |
| 2004/0137473 | A1 | 7/2004 | Wigler et al. |
| 2005/0100900 | A1 | 5/2005 | Kawashima et al. |

FOREIGN PATENT DOCUMENTS

| | | |
|---|---|---|
| EP | 0 665 293 A2 | 8/1995 |
| EP | 0 543 484 B1 | 1/2001 |
| EP | 0 201184 B2 | 8/2004 |
| WO | WO 87/06270 | 10/1987 |
| WO | WO 91/06678 | 5/1991 |
| WO | WO 93/04199 | 3/1993 |
| WO | WO 94/02634 | 2/1994 |
| WO | WO 94/03624 | 2/1994 |
| WO | WO 95/33073 | 12/1995 |
| WO | WO 96/04404 | 2/1996 |
| WO | WO 96/32504 | 10/1996 |
| WO | WO 97/04126 | 2/1997 |
| WO | WO 97/47767 | 12/1997 |
| WO | WO 98/36094 | 8/1998 |
| WO | WO 98/44151 | 10/1998 |
| WO | WO 98/44152 | 10/1998 |
| WO | WO 98/45474 | 10/1998 |
| WO | WO 00/18957 * | 4/2000 |
| WO | WO 00/41524 | 7/2000 |
| WO | WO 00/47767 | 8/2000 |

OTHER PUBLICATIONS

Westin et al., Feb. 2000, Nature Biotechnology, vol. 18, pp. 199-204.*

Walker, Empirical Aspects of Strand Displacement Amplification, PCR Methods Appl. 1993 3: 1-6.*

Adessi et al "Solid phase DNA amplification: characterization of primer attachment and amplification mechanisms," *Nucleic Acids Research* 28 (20): 1-8 (2000).

Dubiley et al "Polymorphism analysis and gene detection by minisequencing on an array of gel-immobilized primers" *Nucleic Acids Research* 27 (18): i-vi (1999).

Strick et al "Stress-Induced Structural Transitions in DNA and Proteins" *Annu. Rev. Biophys. Biomol. Struct.* 29: 523-43 (2000).

Walker et al "Strand displacement amplification—an isothermal, in vitro DNA amplification technique," *Nucleic Acids Research* 20 (7): 1691-1696 (1992).

Walter et al "Strand displacement amplification as an in vitro model for rolling-circle replication: Deletion formation and evolution during serial transfer," *Proc. Natl. Acad. Sci USA* 91: 7937-7941 (Aug. 1994).

Walker et al., Multiplex strand displacement amplification (SDA) and detection of DNA sequences from *Mycobacterium tuberculosis* and other mycobacteria, Nucleic Acids Research, 22:2670-2677 (1994).

Notomi et al., Loop-mediated isothermal amplification of DNA, Nucleic Acids Research, 28:i-vii (2000).

Lizardi et al., Mutation detection and single-molecule counting using isothermal rolling-circle amplification, Nature Genetics,19:225-232 (1998).

Chang et al., PCR Amplification of Chromosome-Specific DNA Isolated from Flow Cytometry-Sorted Chromosomes, Genomics, 12:307-312 (1992).

Gubler et al., A simple and very efficient method for generating cDNA libraries, Gene, 25:263-269 (1983).

Helfman et al., Identification of clones that encode chicken tropomyosin by direct immunological screening of a cDNA expression library, Proc. Natl. Acad. Sci USA, 80:31-35 (1983).

Kalisch et al., Covalently linked sequencing primer linkers (splinkers) for sequence analysis of restriction fragments, Gene, 44:263-270 (1986).

Kimmel et al., Preparation of cDNA and the Generation of cDNA Libraries: Overview, Methods in Enzymology, 152:307-316(1987).

Kinzler et al., Whole genome PCR: application to the identification of sequences bound by gene regulatory proteins, Nucleic Acids Research, 17:3645-3653 (1989).

Lucito et al., Genetic analysis using genomic representations, Proc. Natl. Acad. Sci USA, 95:4487-4492 (1998).

Mueller et al., In Vivo Footprinting of a Muscle Specific Enhancer by Ligation Mediated PCR, Science, 246:780-786 (1989).

Nussbaum et al., Isolation of anonymous DNA sequences from within a submicroscopic X chromosomal deletion in a patient with choroideremia, deafness, and mental retardation, Proc. Natl. Acad. Sci. USA, 84:6521-6525 (1987).

Ochman et al., Genetic Applications of an Inverse Polymerase Chain Reaction, Genetics, 120:621-623 (1988).

Oliphant et al., Cloning of random-sequence oligodeoxynucleotides, Gene, 44:177-183 (1986).

Pfeifer et al., Genomic Sequencing and Methylation Analysis by Ligation Mediated PCR, Science, 246:810-813 (1989).

Saiki et al., Analysis of enzymatically amplified β-globin and HLA-DQα DNA with allele-specific oligonucleotide probes, Nature, 324:163-166 (1986).

Saiki et al., Primer-Directed Enzymatic Amplification of DNA with a Thermostable DNA Polymerase, Science, 239:487-491 (1988).

Sanger et al., Cloning in Single-stranded Bacteriophage as an Aid tp Rapid DNA Sequencing, J. Mol. Biol., 143:161-178 (1980).

Saunders et al., PCR amplification of DNA microdissected from a single polytene chromosome band: a comparison with conventional microcloning, Nucleic Acids Research, 17:9027-9037 (1989).

Steigerwald et al., Ligation-mediated PCR improves the sensitivity of methylation analysis by restriction enzymes and detection of specific DNA strand breaks, Nucleic Acids Research, 18:1435-1439 (1990).

Triglia et al., A procedure for in vitro amplification of DNA segments that lie outside the boundaries of known sequences, Nucleic Acids Research, 16:8186 (1988).

Sterky et al., Direct sequencing of bacterial artifical chromosomes (BACs) and prokaryotic genomes by biotin-capture PCR, Journal of Biotechnology, 60:119-129 (1998).

Cheng et al., Chip PCR. II. Investigation of different PCR amplification systems in microfabricated silicon-glass chips, Nucleic Acids Research, 24:380-385 (1996).

Hahn et al., Quantitative polymerase chain reaction with enzyme-linked immunosorbent assay detection of selectively digested amplified sample and control DNA, Anal, Biochem, 229:236-248 (1995).

Fu et al., Sequencing double-stranded DNA by strand displacement, Nucleic Acids Research, 25:677-679 (1997).

Lockhart et al., Expression monitoring by hybridization to high-density oligonucleotide arrays, Nature Biotechnology, 14:1675-1680 (1996).

Oroskar et al., Detection of immobilized amplicons by ELISA-like techniques, Clinical Chemistry, 42;1547-1555 (1996).

Yershov et al., DNA analysis and diagnostics on oligonucleotide microchips, Proc. Natl. Acad. Sci. USA, 93:4913-4918 (1996).

Velculescu et al., Serial analysis of gene expression, Science, 270:484-487 (1995) (please transfer from U.S. Appl. No. 10/378,688).

Matsunaga et al., Selecting amplifying one fragment from DNA fragment mixture by polymerase chain reaction with a pair of selective primers, Electrophoresis, 17:1833-1840 (1996) (please transfer from U.S. Appl. No. 10/378,688).

Ferguson et al., A fiber optic DNA biosenbsor microarray for the analysis of gene expression, Nature Biotechnology 14:1681-1684 (1996) (please transfer from U.S. Appl. No. 10/378,688).

Pease et al., Light-generated oligonucleotide arrays for rapid DNA sequence analysis, Proc. Natl. Acad. Sci. USA, 91:5022-5026 (1994).

* cited by examiner

Figure 2

```
  1 GGGCCCCCCCTCGAGAAGCCGTGCTGTCAGCATCAGCATCATCGGTGAGACCTCTCCCCA  60

61 AGCCCTACAGACCCTGGGACTAGGGTGCAGGACAGCACAGGCTCTAATTTCCTGCCCCAT 120

121 TCTGGCCTTATCCCTAACAGCCACCCCACCTCTCCCTCCATGCACCCACACCCAAGCCTC 180

181 CCCTACCCCACCCAAATTCTGCCAAGAGAGCAGCCAAGCCTCTCCCTTCTTCCCTCTGAG 240
                                      -------P3------->
241 CTAAAAAAAGGAACAGACGGCTGGGCGCGGTGGCTCACGCCTGTAATCCCAACACTCCAT 300
                                                             <-
301 GCATCTGGTGATGCGAGCTCGACTCTGGGGAAAACACTGGGTTTTCCCAGAGTCGAGCAT 360
    ---P155r-----                           <----P203r----
361 TCTACCTGGGAGGCCAGCTACTTGAGAGGCTGAGGCAGGAGAATTGCTTGAACCCAGGAG 420
    --
421 GCATAGATTGTGATGAGCCAAGATCGCACCATTGCATGCCAGCCTCGGCAACAAAAGTGA 480

481 AACTCCATCTCAAAAAAAAAAGAAAGGGAAAGACTCCACTGGGGCTCCCACTAAATAACC 540
                                                <---P386r--
541 CTCTCTCAACCCGAAGTCTTCCTTTCTGACTGGATCCAACTTTGTCTTCCAGAACCAGGC 600
    -----
601 AGATCCACTAGTTCTAGAGCGGCCGCCACCGCGGTGGAGCTCCAGCTTTTGTTCCCTTTA 660

661 GTGAGGGTTAATTCCGAGCTTGGCGTAATCATGGTCATAGCTGTTTCCTGTGTGAAATTG 720

721 TTATCCGCTCACAATTCCACACAACATACGAGCCGGAAGCATAAAGTGTAAAGCCTGGGG 780
                                        <----P605r-----
781 TGCCTAATGAGTGAGCTAACTCACATTAATTGCGTTGCGCTCA
```

Figure 3
100 micrometers
⟵⟶
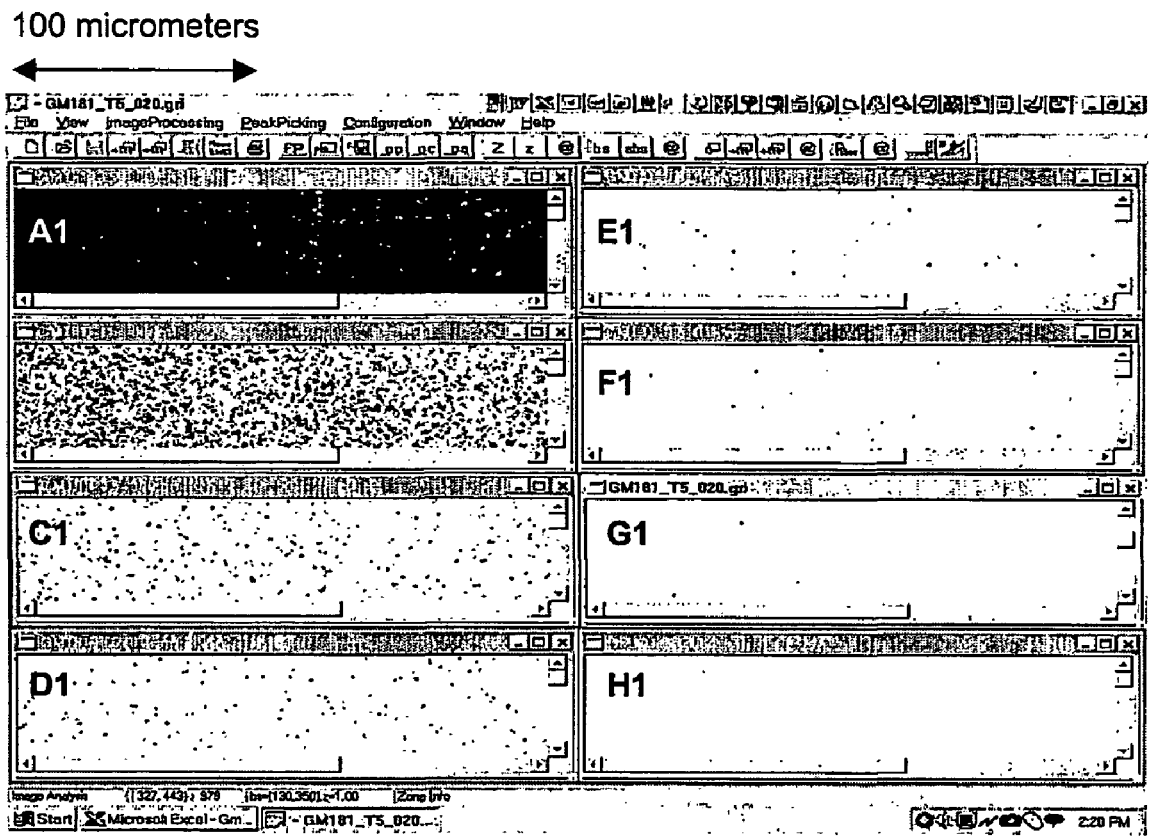
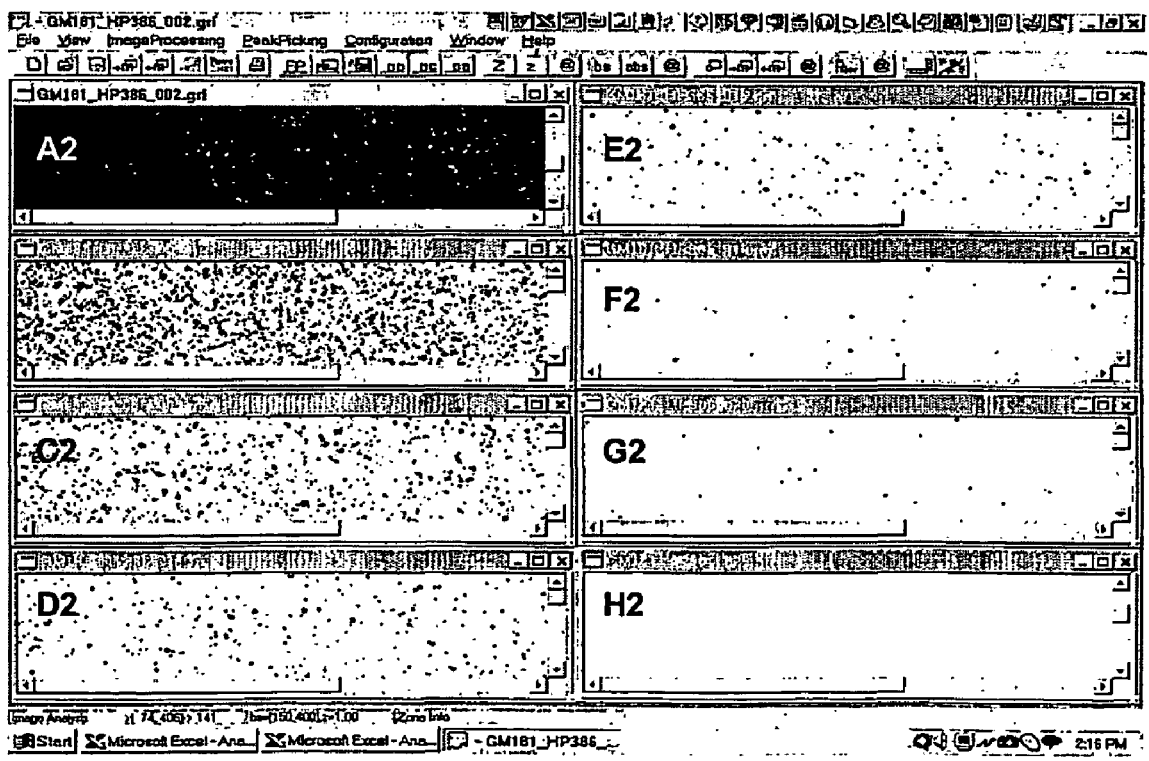

Figure 9
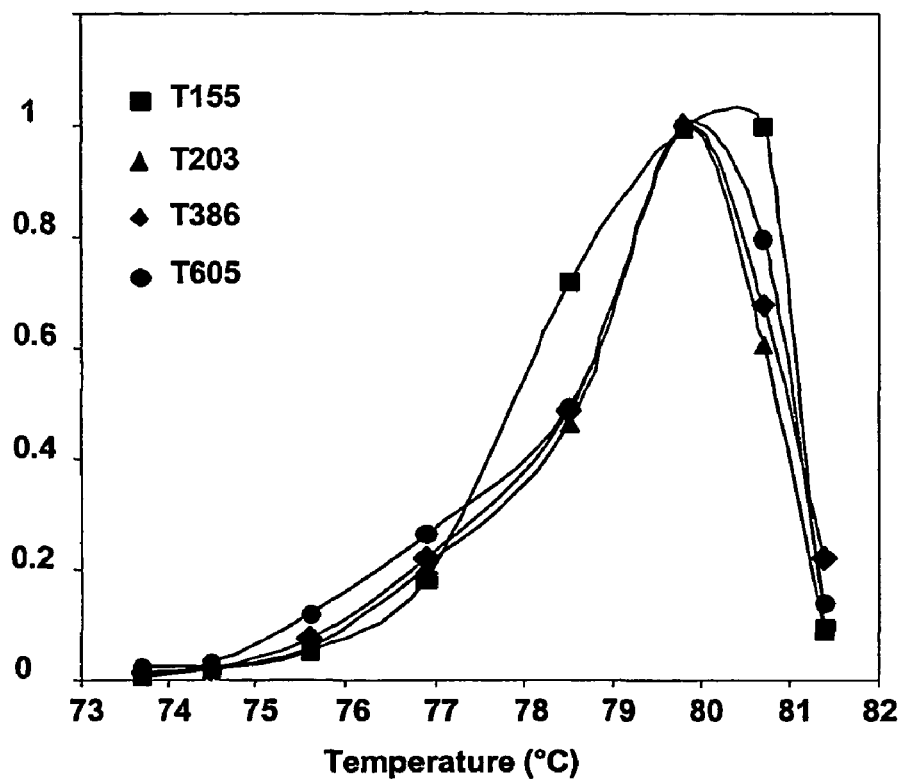
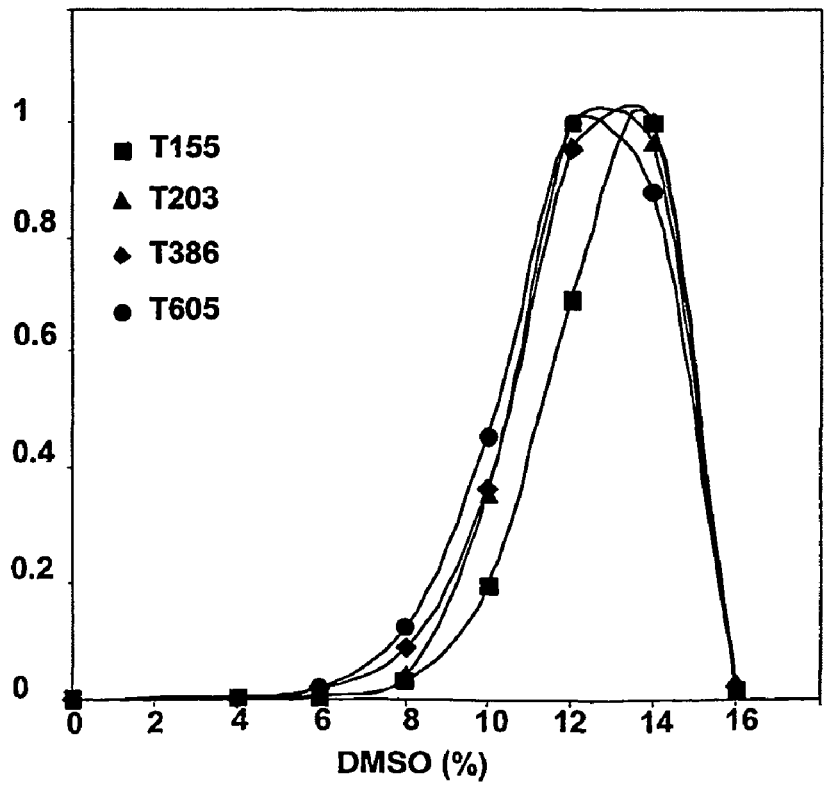

ISOTHERMAL AMPLIFICATION OF NUCLEIC ACIDS ON A SOLID SUPPORT

FIELD OF THE INVENTION

This invention relates to the field of nucleic acid amplification. More specifically, this invention relates to a method for the isothermal amplification of nucleic acids based on the use of a solid surface, and to apparatus and kits useful for applications needing high throughput, in particular nucleic acids sequencing.

BACKGROUND OF THE INVENTION

Nucleic acid sequence analysis has become a cornerstone in many activities in biology, biotechnology and medicine. The ability to determine nucleic acid sequences has become increasingly important as efforts have commenced to determine the sequences of the large genomes of humans and other higher organisms and also, for example, in single nucleotide polymorphisms (SNPs) detection and screening and gene expression monitoring. The genetic information provided by nucleic acid sequencing has many applications, for example, in drug target discovery and validation, disease diagnosis, risk scoring, and organism identification and characterization.

Due to the rapidly increasing demand of reliable data on the genetic information related to an organism, a disease, or to individuals into a population, it is more and more important to improve consequently the throughput of the sequencing methods. The basic objective of such applications is the determination of the sequence of the four bases adenine (A), cytosine (C), guanine (G) and thymine (T) or uracil (U) comprised in the nucleic acids of interest, and belonging to a cell type, to an organism, or to a population of individuals. Most of the nucleic acid sequencing methods (reviewed in Yan H et al., Science 2000, 289 (5486):1890-2) allows the determination of a nucleic acid sequence, either directly (using primer-driven nucleotide extension or hybridization technologies) or indirectly (by electrophoretic and/or cleavage analysis). However, the scientific and economic value of any application dedicated to nucleic acid sequence analysis is highly dependent from the actual throughput of the method.

The efforts necessary to obtain an isolated nucleic acids in a quantity and of a quality acceptable to have reliable results constitute one of the main issues to be considered when evaluating the throughput of a sequencing method. The original sample containing the nucleic acid to be sequenced often does not provide enough material to perform such analysis, unless either relatively high quantity of starting material and/or considerable human intervention are provided. This is particularly important in the case of forensic or archival DNA specimens, or mRNA samples obtained from particular cell types, when sequencing methods needing hundreds of nanograms of an isolated DNA sequence have to be performed starting from nanograms, or less, of total genomic DNA.

To overcome such problem, the solution mainly adopted is to amplify a DNA sequence by generating several copies only of the nucleic acid fragment of interest. In general, the amplification of a nucleic acid needs a series of actions to be repeated:

a) Providing a first nucleic acid (the template) containing the sequence of interest;
b) Providing a second nucleic acid (the primer) containing, at least at its 3' end, a sequence complementary to a sequence contained in the first nucleic acid and adjacent, or internal, to the 3' end of the sequence of interest;
c) Providing the conditions allowing the transition of both template and primer into single stranded molecules, at least in the complementary region of the two nucleic acids;
d) Providing the conditions allowing the hybridization between the complementary sequence located in the template and in the primer;
e) Providing a nucleic acid polymerase able to synthetize the complementary strand of the template region starting from the 3' end of the hybridized primer following the Watson and Crick base pairing rules (A-T, or A-U, and C-G);
f) Provoking the separation of the resulting two stranded nucleic add (one strand belonging to the original template, the other containing the primer fused to the sequence complementary to the region of the template where the nucleotide extension was possible), so that each strand can become the template for another hybridization and polymerization.

Usually, a second primer is also added into the amplification reaction to start the polymerization by hybridizing it to a portion of newly synthetized strand adjacent, or internal, as well to the sequence of interest. If two primers, each specific for one complementary strand, are used, the repetition of these cycles allows the synthesis of multiple copies of both strands of the template sequence comprised between the sequences used to hybridize the primers. Alternatively, if only one primer is provided, multiple copies of a single strand are produced.

The key point is to restore continuously the conditions permitting the dehybridization of the original and the newly synthesized strands and their hybridization to the free primer molecules to restart the polymerization and generate quickly the desired amount of the specific nucleic acid sequence. Primers molecules are generally present at a concentration considerably higher than the template molecules, so that the exponential kinetic of amplification process can be supported.

Commonly, the transition between single stranded and double stranded form of the nucleic acids is obtained by raising and lowering the temperature of the system in which the amplification process is performed. At this scope, the elements necessary for the amplification (template, primers, nucleic acid polymerase, nucleotides, salts) are submitted to a series of heating and cooling phases generated by an external device.

Such approach, usually called thermocycling, is applied in the well-known technique called Polymerase Chain Reaction (PCR; Taylor G R, "Polymerase chain reaction: basic principles and automation" in "PCR: a Practical approach", edited by Mcpherson M J et al., Oxford Univ. Press 1991), in which the following step are conducted in a precise order and for predefined time periods:

a) Denaturation (90° C.-95° C. for 30-60 seconds). The external device provides the energy (in the form of heat) necessary to increase the movement of the nucleic acid molecules at a level sufficient to break the non-covalent interactions stabilizing double stranded configuration. This step can be eventually omitted in the first cycle, if the template and primers are already in a single stranded form, but it is absolutely necessary in all subsequent cycles.
b) Hybridization (35° C.-80° C. for 30-90 seconds). Complementary sequence contained in the primers and in the template molecules can hybridize once that the temperature is lowered. This temperature, which has to be attentively controlled to avoid the hybridization of molecule having only limited homology, is calculated on a case-by-case basis since it is a function of both the length and the C/G content of the nucleic acid sequence into primer and template complementary regions.

c) Elongation (60° C.-85° C. for 60-180 seconds). It is the only step actually producing new nucleic add molecules. The temperature at which elongation is performed is a function of the chosen polymerase and, apart from few exceptions, it does not correspond to the hybridization temperature. Usually the elongation of the newly synthetized strand is completed by the commonly used polymerases in one or few minutes, depending on the length of the nucleic acid to be amplified. New priming events cannot take place until such extended strand is not released, at least partially, as a single stranded molecule from the double stranded molecule resulting from the elongation.

Commonly, in order to obtain a quantity of nucleic acid sufficient for further analysis, these steps are repeated for 15-40 cycles, after which the PCR amplification usually reaches a plateau due to the exhaustion of the polymerase.

Even if many different technologies, strategies, and reaction conditions have been developed on the basic scheme, PCR has severe limitations due to a series of specific requirements:

a) an heating and cooling device;

b) a polymerase which remains highly progressive and accurate even after many cycles at the high temperatures required for the nucleic acid denaturation;

c) the fractionation of the amplification process into many cycles, so that the polymerization is not continuous but synchronized with the thermocycling process. The nucleic acid polymerization reaction cannot be achieved in a continuous way, since it is regularly interrupted to reestablish the conditions necessary for the hybridization between the free primer and template molecules, slowing down the entire process.

Various solutions have been disclosed in the prior art to overcome such limitations of classical PCR, in particular in providing alternative approaches to allow the strand separation and hybridization in isothermal conditions, without thermocycling.

The Strand Diplacement Amplification (SDA) is an isothermal nucleic acid amplification and detection method which makes use of a polymerase in conjunction with an endonuclease that will cut only the polymerized strand such that the polymerase will displace such strand while generating a newly polymerized strand (EP 497272; Walker G T, PCR Methods Appl 1993, 3 (1):1-6). This technique, based on the repetition of the single strand nicking, extending and displacing steps, has been variously adapted (WO 96/23904; Westin L et al., Nat Biotechnol 2000, 18(2):199-204), but such approach has a limited applicability. An endonuclease must be added together with the polymerase, and therefore the range of allowed temperatures at which the whole process can be performed is restricted to the one maintaining the activity of both enzymes. In the case of endonucleases, such range (usually 25° C.-50° C.) is usually too low to avoid non-specific hybridization of the primers to the template, leading to a considerable proportion of reactions which are nonproductive or generate undesired products. Moreover, the nucleic acids acting as primers and/or templates may have to be additionally modified, since it is mandatory that the endonucleolytic recognition site has to be absent from the template region to be amplified, while it has always to be present into the primer sequence.

The Rolling Circle Amplification (RCA) is a technique making use of a DNA polymerase elongating circularized oligonucleotide probes under isothermal conditions with either linear or geometric kinetics, and generating tandemly linked copies of the DNA molecule to amplify as a consequence of a complex pattern of strand displacement events (Walter N G and Strunk G, Proc Natl Acad Sci USA 1994, 91 (17): 7937-41; WO 94/03624). Also in this case, even if the technology has been variously adapted (WO 97/19193, Isaksson A and Landegren U, Curr Opin Biotechnol 1999, 10(1): 11-5), such techniques have several limitations like, for instance, the use of circularized molecules and the production of the amplified molecules not as single entities but as a series of molecules containing a variable number of copies of the original sequences, tandemly linked to each other.

Other techniques have been developed to solve the problem through an intermediate DNA-RNA hybrid in an isothermal, multienzyme reaction containing an RNA polymerase, a ribonuclease and a reverse transcriptase (WO 91/04340, WO 92/08800, WO 97/04126; Gebinoga M and Oehlenschlager F, Eur J Biochem 1996, 235 (1-2): 256-61). It is evident that several problems can be encountered using these methods, related both to the rapid RNA degradation and to the complexity of finding the conditions to make all the components work correctly in the reaction at the same time, maintaining the specificity and the speed of the amplification process.

Even if the amplification technologies are instrumental in the analysis of very small amount of nucleic acid sequences, the throughput of nucleic acid sequencing methods is linked not only to the availability of isolated nucleic acids in an amount sufficient to be processed and obtain reliable information, but also to the possibility to process several samples quickly and with limited human intervention. Most of the genetic information is still now generated using technologies, like gel electrophoresis, which are cumbersome, labour intensive, difficult to automate, and require relatively large devices. Moreover, such methods generally allow only the individual processing of each nucleic acid entity to be sequenced. Therefore, many technologies were developed to provide specific solutions to allow the parallel analysis of several different nucleic acids.

In the prior art, a common way to increase throughput is the processing of many samples in parallel using a solid support, often defined as "DNA microarray" or "DNA chip", on which nucleic acid are immobilized and then analyzed using different approaches involving either labeled single nucleotides or labeled nucleic acids (Southern E et al., Nat Genet. 1999, 21(1 Suppl): 5-9; Lockhart D J and Winzeler E A, Nature 2000, 405 (6788): 827-36). Large molecules (e.g. molecules over 500 nucleotides long) as well as smaller molecules such as oligonucleotide primers, can be efficiently linked to a solid support in a covalent manner by physical or chemical means, either non-specifically or using a specific chemical group at one end (Adessi C et al., Nucleic Acids Res 2000, 28(20):E87; Okamoto T et al., Nat Biotechnol 2000, 18(4): 43841). The combination of suitable robotics, micromechanics-based systems, and microscopical techniques makes technically feasible the ordered deposition and analysis of up to millions of nucleic acids per $cm^2$ of support.

Using similar approaches, a primer extension reaction can be obtained by immobilizing either the primers or the template molecules (WO 91/13075, WO 00/47767). Alternatively, primers can be grafted to a surface and, in conjunction with free primers in solution, allow the amplification and attachment of a PCR product onto the surface (Andreadis J D and Chrisey L A, Nucleic Acids Res 2000, 28(2): e5). Primers can be also immobilized on a matrix and the template molecules be kept in the liquid phase in a range of temperature (58° C.-74° C.) allowing, in a very random and uncontrolled way, an equilibrium between single/double stranded forms, as well as a single base extension (Dubiley S et al., Nucleic Acids Res 1999, 27(18): e19).

The main disadvantage of these technologies is that, for each application, a DNA chip has to be designed and manufactured first, an operation still quite lengthy, complex, and expensive, and therefore it can be afforded only when very large numbers of the chip are required. Moreover, the chips can be often used only for hybridization and/or single base elongation, are not reusable, and for each chip only one sample of nucleic acids can be processed at each time (Cheung V G et al., Nat Genet. 1999, 21(1 Suppl):15-9; Bowtell D D, Nat Genet. 1999, 21(1 Suppl): 25-32).

Other technologies were recently developed at the scope to solve, at least partially, the problems related to the amplification and the sequencing throughput by coupling the two processes more effectively.

WO 96/04404 (Mosaic Technologies Inc.) discloses methods of detection of a target nucleic acid potentially contained in a sample. The method involves the induction of a PCR based amplification of a target nucleic acid only when the target nucleic acid is present in the sample being tested. Specific primers are attached to a solid support, allowing the amplified target nucleic acid sequences also to be attached to such support. The two strand-specific primers are, as for conventional PCR, specifically designed so that they hybridize sequences flanking, or internal, to the target sequence to be amplified and drive the standard thermocycling process.

The first step in this PCR-based amplification process is the hybridization of the target nucleic acid to the first specific primer attached to the support ("primer 1"). A first elongation product, which is complementary to the target nucleic acid, is then formed by extension of the primer 1 sequence. On subjecting the support to the high temperatures necessary for strand dehybridization, the target nucleic acid is released and can then participate in further hybridization reactions with other primer 1 sequences which may be attached to the support. The first attached elongation product may then hybridize with the second specific primer ("primer 2"), attached as well onto the support and a second elongation product complementary to the first one can be formed by extension of the primer 2 sequence and is also attached to the support. Thus, the target nucleic acid and the first and second elongation products are templates molecules capable of participating in a plurality of hybridization and extension processes, limited only by the initial presence of the target nucleic acid and the number of primer 1 and primer 2 sequences initially present. The final result is a number of copies of the target sequence attached to the surface.

The amplification technique disclosed in this document is generally called as "Bridge Amplification" since, after the first cycle when the template is in solution, both template and primer molecules are immobilized on the support through their 5' end, forming therefore a typical bridge-like structure when they hybridize.

Since this amplification process allows the immobilization only of the target nucleic acid, the monitoring of the support allows a generically qualitative evaluation of the presence or absence of a specific target sequence predefined by the operator when designing the primers. The Bridge Amplification can be used, therefore, as an high throughput sequence analysis method if different sets of first and second primers are arrayed on different regions of the solid support, and if it is not desired a base-by-base analysis of the target sequence. Moreover, such technology can provide a substantial improvement in the serial analysis of different sequences and/or samples only if primers specific for each different target sequence are known and can amplify the target sequence in similar amplification conditions.

Other technologies try to exploit more effectively the mechanism underlying the Bridge Amplification. WO 98/44151 (Glaxo) discloses how, by engineering all the nucleic acid templates to be analyzed with the addition, at both extremities, of linker sequences complementary to the immobilized primers, each template molecule in solution can be randomly arrayed and amplified, irrespectively of their actual sequence. In this way, identical PCR amplification products are immobilized at high density in a discrete area of the solid support, which is called "DNA colony", due to the similarity to bacterial colonies when they are observed on a plate. Each DNA colony can be visualized and analyzed singularly, for example, by hybridization with labeled reference sequences or by using a primer elongation-based approach. WO 00/18957 (Appl. Res. Syst.) discloses how the efficacy of the Bridge Amplification technology is improved by immobilizing simultaneously both primer and template molecules on the solid support before that amplification actually begins.

A substantial limitation of technologies based on Bridge Amplification is that, whatever specificity of primer sequences or immobilization strategy is chosen, there is no teaching on how to perform the process in isothermal condition (i.e. without the necessity of a thermocycling process) and therefore, they still suffer from the same limitations associated to PCR. Even if it is possible to apply a reduced number of cycles, due to the sensibility of the analysis and visualization systems, there is the additional complication that dehybridization temperature can affect the uniformity of the solid support, as well as the stability of the nucleic acids binding with the surface. However, none of the isothermal amplification systems disclosed in the prior art achieves, at the same time, the density of different template molecules, which can be amplified and analyzed simultaneously, and the self-sufficiency characterizing the Bridge Amplification technology.

It would be therefore advantageous to devise a method where the primer hybridization, strand elongation and strand separation happen in a continuous fashion, at constant temperature, applying the principles of Bridge Amplification. Actually, the more critical point is to obtain the strand separation, since only the temperature or the use of complex and specific techniques have been disclosed in the prior art to solve the problem. WO 97/47767 (Sarnoff Corp.) suggested the use of chemical or electrostatic based denaturation procedures applied to amplification processes. However, such procedures needs highly dedicated materials, like an electric field generating device, or chemicals, like NaOH, poorly compatible with common amplification procedures and requiring specific additional steps (i.e. modifying primers, washing away the chemicals before restarting the elongation).

The Bridge Amplification technology would provide further advantages if it would be possible to trigger simply the strand separation in isothermal conditions, provided that strand separation would be possible only after that elongation has been completed or, if not completed, without disturbing the nucleic acid polymerase completing the elongation.

SUMMARY OF THE INVENTION

It has now been discovered that the strand separation of a double stranded nucleic acid, immobilized by the 5' end of both strands onto the same solid support, can be easily obtained in isothermal conditions if the length of the nucleic acid limits the possibility to be bent. This biophysical feature has been successfully exploited to generate isothermally DNA colonies using the Bridge Amplification.

DESCRIPTION OF THE FIGURES

FIG. 2: sequence of the template T1 plasmid insert. The sequences used to hybridize the different primers and amplify the specific templates tested in the examples are underlined. The primer name and direction of the extension are indicated in the upper line.

FIG. 3: screen copies of the digital inverted images of fluorescently stained, solid-support isothermally amplified nucleic acids, observed with an epifluorescence microscope equipped with a CCD camera. The scale of the images is shown on the top left of the figure.

FIG. 9: variation of the amount of fluorescence obtained by performing the isothermal amplification using different temperatures (A) or DMSO percentages (B) using templates of various length. Each curve has been normalized relative to its highest value.

DETAILED DESCRIPTION OF THE INVENTION

The flexibility of a macromolecule is traditionally measured as persistence length, that is, the minimal size a macromolecule must have in order it can be bent without modifying significantly its local structure. In the salt concentrations compatible with nucleic acid polymerases activity, such length corresponds approximately to 5 nanometers (or to 15 bases) for a single stranded DNA, and approximately to 50 nanometers (or to 150 base pairs) for a double stranded DNA (Tinland B et al., Macromolecules 1997, 30 (19): 5763-5765; Williams L D and Maher L J, Annu Rev Biophys Biomol Struct 2000, 29, 497-521). In other words, double stranded DNA, due to the large number of non-covalent interaction stabilizing its structure, is much stiffer than single stranded DNA. Similar observation were made also for RNA, even though the estimation of the persistence length for double stranded RNA differs in the literature from 35 to 72 nanometers (Zacharias M, Biopolymers 2000, 54(7): 547-60; Kebbekus P et al., Biochemistry 1995. 4; 34(13): 4354-7). Therefore, when external conditions impose a curvature, a double stranded molecule will experience a much higher mechanical stress than a single stranded molecule.

Many biophysical studies tried to quantify and make previsions on the destabilizing effects of the energy resulting from mechanical stress on the non-covalent interactions present into a double stranded DNA, which can be consequent to transcription, supercoiling, or mechanical separation of contiguous 5'/3' extremities (reviewed in Strick T R et al., Annu Rev Biophys Biomol Struct. 2000, 29, 523-43.). Such single/double stranded nucleic acid transitions have been also shown as natural and not controlled phenomena when a double stranded molecule is exposed to temperatures near to the denaturating temperature (Dubiley S et al., Nucleic Acids Res. 1999, 27(18): e19). However, it has never been demonstrated that such phenomena can be induced and usefully exploited if both 5' ends of (partially or completely) double stranded DNA molecules are simultaneously immobilized on a solid support. Moreover, none of them, as well as none of the document describing Bridge Amplification related technologies, suggested that such energy can be willingly induced to avoid thermocycling when performing Bridge Amplification.

Figure 1:
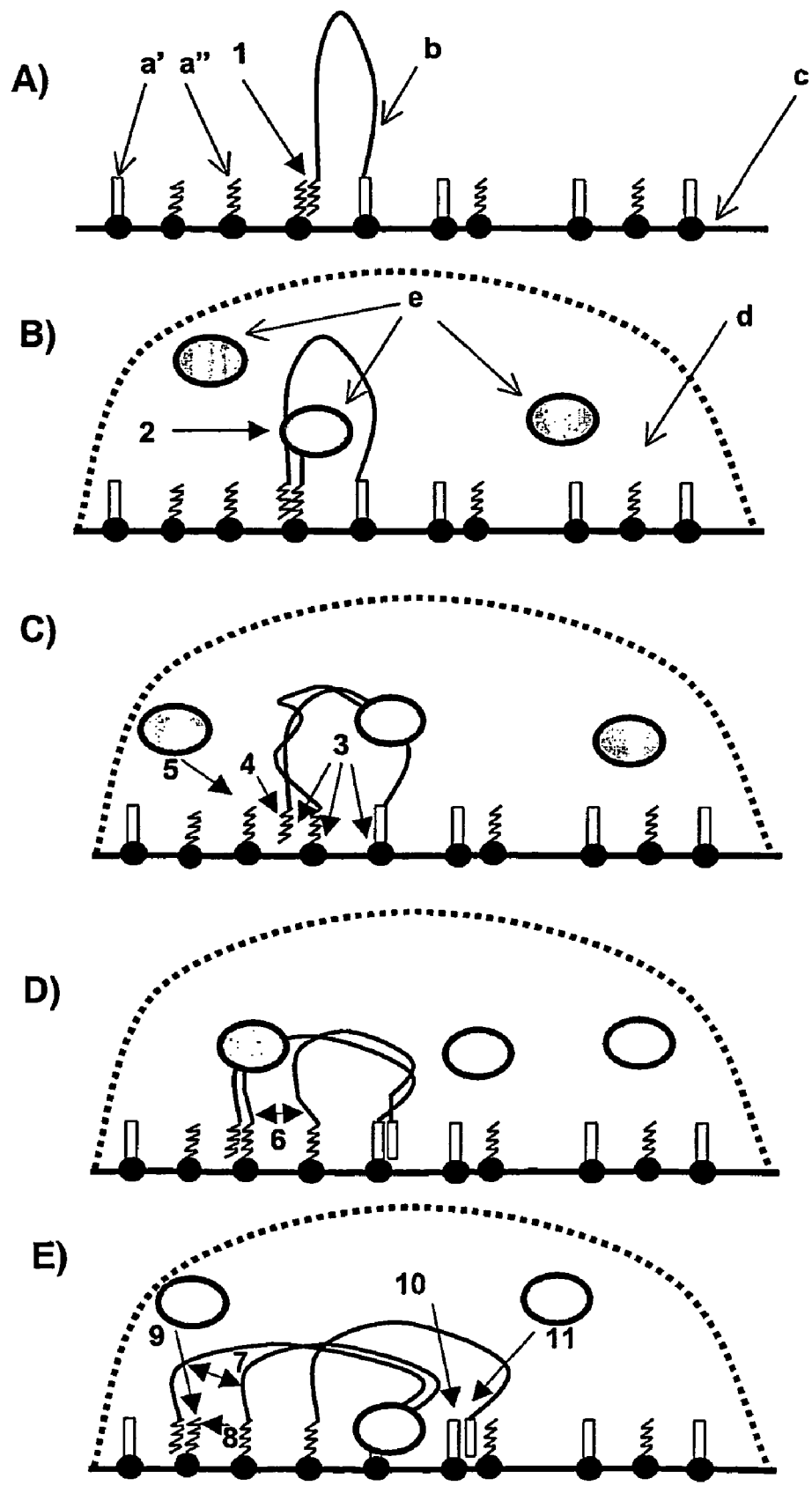
FIG. 1: schematic description of the mechanism underlying the isothermal amplification on solid supports. Letters and numbers refer to actions and components defined in the description of the invention.

FIG. 1 summarizes the molecular mechanisms underlying the present invention.

When the complementary sequences belonging to single stranded primers (a' and a") and templates (b) immobilized the 5' end onto a solid support (c) are dose enough to hybridize (1), each primer/template hybridization product is more or less strongly curved, depending from the distance between the immobilized 5' ends (FIG. 1A).

In the presence of the amplification solution (d), a nucleic acid polymerase molecule (e) can start the extension of a new strand, which is a copy of the immobilized template, from the 3' end of the hybridized primer (2). The double stranded region is consequently extended from the initial hybridization region, and the complex contains a progressively increasing amount of artificially curved, double stranded nucleic acid (FIG. 1B).

During the extension, the double stranded segment distal to the polymerase can be denatured spontaneously as an effect of the mechanical stress induced by the contrast between the stiffness of the double stranded conformation and the curvature imposed by the fixed position of the 5' end of both strands (3). The non-covalent interactions stabilizing the double stranded nucleic acid can generate a consistent mechanical stress if the template is not long enough to accommodate such stiffer structure into the curved configuration. The double stranded part of the molecule can less and less accept the imposed curvature with the growing number of non-covalent interaction present into the molecule, and the mechanical stress can be eliminated only by reducing the portion of the template into a double stranded configuration. At this moment, the portion more weakly associated, and therefore more easily absorbing such stress, is the 3' end of the template molecule, distal to the progressing nucleic acid polymerase, which can become single stranded. The curvature-induced stress is consequently reduced and the polymerase can proceed further until the stress is again too strong to be absorbed. While this process is ongoing, therefore, the double stranded nucleic acid molecules is progressively "unzipped", leaving a 3' end available for hybridizing with another primer (4) and a second DNA polymerase molecule can initiate a second copy of the template (5). This process may take place even as a base by base process. The mechanical stress activated strand opening over 1~2 base(s) at the 3' end of the template could be concomitant with 1~2 base(s) incorporation by the polymerase at the 3' end of the neo-synthesized strand (FIG. 1C).

Once that the first copy of the template is completed, or is going to be completed, the DNA polymerase synthetizing the second copy is capable to induce as well a mechanical stress on the shared strand, which can be progressively separated and displaced from the first synthetized strand (6; FIG. 1D).

The reaction can then proceed up to completion, i.e., the two strands of the template are both immobilized and likely to initiate amplification as described previously. Once that also the second copy of the template is completed, or is going to be completed, the 5' single stranded end of the template can be released (7) and hybridize with another immobilized primer in the proximity (8), while another nucleic acid polymerase molecule can restart synthesis (9). At the same time, the first single stranded copy can hybridize with another primer (10) and initiate a new copying event (11). This process, as shown in FIG. 1E, allows neo-synthesized copies to be continuously turned into single stranded nucleic acids by a mechanical stress-driven strand separation and displacement, which can be reproduced by any immobilized template molecule hybridizing with an immobilized primer, without any externally generated cycling activity.

The present invention shows that the flexibility features of nucleic acids, which are considerably different if the nucleic acid is either in a single stranded or in a double stranded form, allow the templates to be partially released as a single stranded molecule while the polymerization is still ongoing. Surprisingly, the present invention shows also that this event does not affect the activity of the polymerase, but it can be used to drive the isothermal amplification of a template molecule into newly synthetized molecules, all immobilized in a discrete area of a solid surface.

The improvement to the Bridge Amplification method disclosed in the present patent application allow the exponential production of complementary sequences having mixed single/double stranded configurations in a discrete area of a solid support, as for the DNA colonies disclosed in WO 98/44151 and WO 00/18957 but isothermally and in a continuous manner. When the quantity of identical amplified molecules is considered as sufficient, sequencing and other analytical methods described in those patent applications can be equally applied on the DNA colonies generated isothermally either on the support itself, or on molecules released from DNA colonies into solution by methods disclosed in the prior art.

The continuity of the amplification process disclosed in the present invention, coupled with the isothermal conditions, provides evident advantages towards prior art in terms of time and effort savings in order to obtain nucleic acids molecules in a form and in a quantity allowing the applicability of high throughput sequencing methods. It has to be pointed out also that the present invention discloses the use of a solid support not only as a tool to allow the parallel a posteriori analysis of amplified molecules (well known in the prior art), but as a component essential for performing nucleic acids amplification as a continuous process in isothermal conditions.

Even though the persistence length for a double stranded DNA corresponds to 150 base pairs, the methods of the invention proved to be workable on a wide range of DNA or RNA template lengths, in the order of several hundreds of nucleotides. It can be inferred that such range could be further extended to templates containing up to 1000 nucleotides, using conditions identified by the means of the same empirical methods disclosed in the examples of the present patent application for DNA molecules containing from 68 to 605 nucleotides.

The main object of the presents invention is to provide a method for the isothermal amplification of at least one nucleic acid segment containing up to 1000 nucleotides comprising the following steps:

a) forming at least one nucleic acid template comprising the nucleic acid(s) to be amplified, wherein said nucleic acid(s) contains at the 5' end an oligonucleotide sequence Y and at the 3' end an oligonucleotide sequence Z and, in addition, the nucleic acid(s) carry, at the 5' end, the means for immobilizing said nucleic acid(s) onto a solid support;

b) forming one or more colony primers X, which can hybridize either to the oligonucleotide sequence Z or to the oligonucleotide sequence Y and carries, at the 5' end, the means for immobilizing said colony primers to a solid support;

c) mixing said nucleic acid template(s) and colony primers together with a solution allowing their immobilization by the 5' end on a solid support in the presence of said solid support, so that the 5' ends of both the nucleic acid template(s) and the colony primers are bound to said solid support;

d) applying an amplification solution, containing at least a nucleic acid polymerase and nucleotide precursors, to said solid support to generate and immobilize isothermally nucleic acids having sequence identical or complementary to the sequence of the immobilized nucleic acid template(s).

The method of the invention have been successfully performed for amplifying, isothermally and on a solid support, single stranded DNA molecules containing from 68 to 605 bases.

The quantity of immobilized nucleic acids in step c) determines the average number of DNA colonies per surface unit which can be created by the means of the present invention. The ranges of preferred concentrations of the DNA molecules to be immobilized have been determined in the examples as being between 1 nanoMolar and 0.01 nanoMolar for the template molecules, and between 50 and 1000 nanoMolar for the colony primers. Such concentrations of nucleic acids allow the generation of DNA colonies with a density of 1000-100000 for $mm^2$.

The constant temperature applied to the amplification method described in the invention is the temperature at which the nucleic acid polymerase of choice shows an optimal activity. The examples will show that nucleic acid polymerases commonly used for nucleic acid amplification system known in the prior art can be also used to perform the method of the invention at temperature comprised between 70° C. and 85° C. or, more preferably, between 77° C. and 81° C. This range is functional also for the hybridization, since non-specific primer-template hybridization events are generally reduced at these temperatures.

"Isothermal" as used herein is equivalent to "essentially the same temperature", meaning that any deviation from the temperature, initially chosen to perform the method with a specific nucleic acid polymerase, is in the range of the deviation of a commercial thermostat.

"Solid support" as used herein refers to any solid surface to which nucleic acids can be attached, such as for example latex beads, dextran beads, polystyrene surfaces, polypropylene surfaces, polyacrylamide gel, gold surfaces, glass surfaces and silicon wafers. Preferably the solid support is a glass or a polystyrene surface.

"Nucleic acid template" as used herein refers to an entity comprising the nucleic acid (DNA or RNA) to be amplified, and it is present into the reaction as a single, a double, or mixed single-double stranded nucleic acid. The nucleotides making up the nucleic acid templates may be naturally occurring or non-naturally occurring nucleotides.

"Colony primer" as used herein refers to an entity which comprises an oligonucleotide primer which can be immobilized onto a solid surface using its 5' end, and it is capable of hybridizing to a complementary sequence using its 3' end to initiate a specific polymerase reaction.

"Degenerate primer sequences" as used herein refers to a short oligonucleotide sequence which is capable of hybridizing to any nucleic acid fragment independent of the sequence of said nucleic acid fragment.

"Means for immobilizing nucleic acids to a solid support" as used herein refers to any chemical or non-chemical attachment method including chemically-modifiable functional groups. "Attachment" relates to immobilization of nucleic acid on solid supports by either a covalent attachment or a non-covalent attachment "Chemically-modifiable functional group" as used herein refers to a group such as for example, a phosphate group, a carboxylic or aldehyde moiety, a thiol, or an amino group.

"Nucleic acid colony" as used herein refers to a discrete area comprising multiple copies of two complementary nucleic acid strands.

"Derivatised surface" as used herein refers to a surface which has been modified with chemically reactive groups, for example amino, thiol or acrylate groups.

"Functionalised surface" as used herein refers to a derivatised surface which has been modified with specific functional groups, for example maleic or succinic functional moieties.

Nucleic acids which may be amplified according to the methods of the invention include DNA, for example, genomic DNA, complementary DNA, recombinant DNA or any form of synthetic or modified DNA. Their length may vary amongst template molecules simultaneously immobilized on the same solid support, and they may be fragments or smaller parts of larger nucleic acid molecules having a known or unknown sequence. The nucleic acids to be amplified may be derived from any source (e.g., genomic DNA fragments obtained by limited restriction enzyme digestion). However, they may need to be further processed before being used in methods of the invention using standard genetic engineering techniques, as summarized in WO 00/18957, in particular to add the Y and Z sequence necessary to hybridize with colony primers. In the case of mRNA, the isolated mRNA can be transformed into cDNA by the use of a reverse transcriptase and, eventually, into double stranded DNA before being adapted for the methods of the invention.

Alternatively, whenever the template is a natural, synthetic, or modified RNA molecule, it can be directly amplified by the method of the invention using specific enzyme known in the art that can generate double stranded RNA starting from single stranded RNA.

The nucleic acid templates of the invention not only comprise the nucleic acid to be amplified but also the oligonucleotides sequence Y and Z which have a known sequences and can be of variable length. Oligonucleotide sequences Y and Z for use in the methods of the present invention are preferably at least five nucleotides in length, preferably between 5 and 100 nucleotides in length and more preferably of approximately 20 nucleotides in length.

The oligonucleotide sequences Y and Z of the invention may be prepared using techniques which are standard or conventional in the art, or may be purchased from commercial sources. If there are a plurality of nucleic acid sequences to be amplified then the attachment of oligonucleotides Y and Z can be carried out in the same or different reactions.

The oligonucleotide sequences Y and Z contained at the 5' and 3' ends respectively of a nucleic acid template need not be located at the extreme ends of the template. For example although the oligonucleotide sequences Y and Z are preferably located at or near the 5' and 3' ends (or termini) respectively of the nucleic acid templates (for example within 0 to 100 nucleotides of the 5' and 3' termini), they may be located further away (e.g. greater than 100 nucleotides) from the 5' or 3' termini of the nucleic acid template, provided that the sequences Y and Z flank a nucleic acid sequence which is to be amplified not longer than 1000 bases.

Once a nucleic acid template has been prepared, it may be amplified before being used in the methods of the present invention. Such amplification may be carried out using methods well known and documented in the art, for example by inserting the template nucleic acid into an expression vector and amplifying it in a suitable biological host, or amplifying it by PCR. However, this amplification step is not essential, as the method of the invention allows multiple copies of the nucleic acid template to be produced in a nucleic acid colony generated from a single copy of the nucleic acid template, and it can be performed just to introduce the 5' chemically modified immobilizing group, as shown in the examples.

Eventually, the nucleic acid template can be immobilized on the solid support as a double stranded molecule, but it can be made into a single stranded form using methods which are well known and documented in the art, for example by heating to approximately 94° C. and quickly cooling to 0° C. on ice or rinsing in 0.1~0.5 M NaOH.

The sequence(s) comprised into the colony primer and complementary to the oligonucleotide sequences comprised in the template(s) are chosen such that they have the maximal hybridizing activity with its complementary sequence and very low non-specific hybridizing activity to any other sequence. The colony primer can be 5 to 100 bases in length, but preferably 15 to 25 bases in length. Naturally occurring or non-naturally occurring nucleotides may be present in the primer.

One or two different colony primers may be used to generate nucleic acid colonies in the methods of the present invention. In a basic embodiment, two different colony primers, X' and X" are mixed with the nucleic acid template(s) in step c), and the sequences of colony primers X' and X" are such that the oligonucleotide sequence Z can hybridize to one of the colony primers X' and the oligonucleotide sequence Y is the same as one of the colony primers X". Alternatively, the oligonucleotide sequence Z is complementary to oligonucleotide sequence Y, and colony primer X is of the same sequence as oligonucleotide sequence Y.

When producing the nucleic add templates and primers of the invention additional desirable sequences can be introduced by methods well known and documented in the art. Such additional sequences include, for example, restriction enzyme sites, modified nucleotides, or other nucleic acid tags enabling the identification and/or isolation of amplification products containing a given nucleic acid template sequence. Other desirable sequences include fold-back DNA sequences (which form hairpin loops or other secondary structures when rendered single-stranded), 'control' DNA sequences which direct protein/DNA interactions, such as a promoter, an enhancer, a replication origin, or an operator DNA sequence which are recognized by specific DNA-binding proteins.

The colony primers of the present invention may also include degenerate primer sequences. Such degenerate primers thus do not require the presence of oligonucleotide sequences Y or Z in the nucleic acid template(s) for hybridization to the template to occur, although the use of degenerate primers to hybridise to a template containing the oligonucleotide sequences X or Y is not excluded. However, for use in the amplification methods of the present invention, the degenerate primers must hybridise to nucleic acid sequences in the template at sites located on both sides, or flanking, the nucleic acid sequence which is to be amplified.

The 5' end of the nucleic acid template and primers prepared as described above is modified to carry the means of immobilizing the 5' ends of both the nucleic acid template(s) and the colony primers. The immobilization of the nucleic acids using the 5' end leaves the 3' end remote from the support such that the 3' region of templates and primer can hybridize and drive the synthesis of a new strand.

The immobilization protocol should avoid the release of templates and primers from the solid surface during the isothermal amplification. Therefore, the means for immobilization are preferably chemically modifiable functional groups which allow the formation of a covalent binding between said molecules and a solid support having a derivatised surface, which is subsequently modified with bifunctional crosslinking groups to provide a functionalized surface. Alternatively, the immobilization can be obtained by irreversible passive adsorption or by exploiting the affinity between specific molecules (for example, immobilization on an avidin-coated surface by biotinylated molecules).

Examples of chemically modifiable functional groups to be added at the 5' end of the nucleic acids to be immobilized are thiol, hydroxyl, dimethoxyltrityl (DMT), amino, or phosphate groups, as well as carboxylic or aldehyde moieties. Examples of crosslinking agents useful to derivatise a solid support are 1-ethyl-3-(3-dimethylaminopropyl)-carbodiimide hydrochloride (EDC), succinic anhydride, phenyldiisothiocyanate or maleic anhydride, or a hetero-bifunctional crosslinker such as for example m-maleimidobenzoyl-N-hydroxysuccinimide ester (MBS), N-succinimidyl[4-iodoacethyl] aminobenzoate (SIAB), Succinimidyl 4-[N-maleimidomethyl]cyclohexane-l-carboxylate (SMCC), N-γ-maleimidobutyryloxy-succinimide ester (GMBS), Succinimidyl-4-[p-maleimidophenyl] butyrate (SMPB) and the sulfo (water-soluble) corresponding compounds. Most preferably, the nucleic acid templates and primers are modified with thiol, phosphate or amino group at the 5' end modification and immobilized using an immobilization solution containing 1-ethyl-3-(3-dimethylaminopropyl)-carbodiimide hydrochloride (EDC) as crosslinking agent.

Although the solid support may be any solid surface to which nucleic acids can be immobilized, such as for example latex or dextran beads, polystyrene surfaces, polypropylene surfaces, polyacrylamide gel, gold surfaces, glass surfaces and silicon wafers, preferably the solid support is rigid enough to be not affected by the force deployed during the elongation and allowing a covalent attachment of the nucleic acid through functionalization using mono- or bifunctional crosslinking reagents, as described before and in WO 00/18957. Once both the nucleic acid templates and colony primers of the invention have been synthesized, or purified from a sample, and modified as described previously, they can be mixed together at concentrations calculated taking into account the data showed in this patent application, as well as the desired density of DNA colonies. Preferably the concentration of the template is sub-nanoMolar and colony primers are 50-100000 times more concentrated.

Once that colony primers and nucleic acid templates have been immobilized on the solid support, DNA colonies of the invention can then be generated by carrying out the isothermal amplification reaction, as depicted in FIG. 1, so that each colony comprises multiple copies of the original immobilized nucleic acid template and its complementary sequence. The boundary of the nucleic acid colony formed is limited to a relatively local area to the area in which the initial template nucleic acid was immobilized. Clearly, once more copies of the template molecule and its complement have been synthetized by carrying out the amplification method of the invention, then the boundary of the nucleic acid colony being generated will be able to be extended further, although the boundary of the colony formed is still limited to a small portion of the solid support whereon the nucleic acids were immobilized.

The size and the number of DNA colonies can be controlled by modulating the time during which the solid support is subjected to the isothermal amplification. Thus the number of nucleic acid colonies formed on the surface of the solid support is dependent upon the number of nucleic acid templates which are initially immobilized to the support, providing there is a sufficient number of immobilized colony primers at a distance allowing the hybridization with template molecules. By controlling the initial density of the nucleic acid templates and primers, an optimum situation can be reached wherein a high density of individual nucleic add colonies can be produced isothermally on a solid support of a size sufficient to allow their analysis and containing a large enough number of amplified sequences.

The isothermal amplification disclosed in the present patent application can be performed using a DNA- or a RNA-dependent DNA polymerase, plus a supply of nucleoside triphosphate molecules or any other nucleotide precursors, for example modified nucleoside triphosphate molecules.

Examples of nucleic acid polymerases which can be used in the present invention are DNA polymerase (Klenow fragment, T4 DNA polymerase), thermostable DNA polymerases (Perier F. B. et al., Adv. Protein Chem. 1996, 48:377-435) identified and cloned in a variety of thermostable bacteria (such as Taq, VENT, Pfu, Tfl DNA polymerases) as well as their genetically modified derivatives (TaqGold, VENTexo, Pfu exo). Preferably the nucleic acid polymeras used for colony primer extension is stable under temperature at which the primer and template hybridization results enough specific to avoid incomplete or spurious amplifications of the template.

The amplification solution contains preferably, as nucleotide precursors, deoxyribonucleotide triphosphates, for example dATP, dTTP, dCTP, dGTP, naturally or non-naturally occurring, for example modified with a fluorescent or radioactive group. A large variety of synthetically modified nucleic acids have been developed for chemical and biological methods in order to increase the detectability and/or the functional diversity of nucleic acids. These functionalized/modified molecules can be fully compatible with natural polymerizing enzymes, maintaining the base pairing and replication properties of the natural counterparts, as recently reviewed (Thum O et al., Angew. Chem. Int. Ed. 2001, 40 (21): 3990-3993).

When the template is either a RNA or a DNA molecule and it is desired to obtain amplification products in the form of double stranded RNA, the nucleic acid polymerase can be a RNA- or a DNA-dependent RNA polymerase, for example a viral RNA replicase or a ribozyme (Johnston W K et al., Science 2001, 292(5520):1319-25; Tayon R Jr et al., Nucleic Acids Res 2001, 29(17):3576-82). The amplification solution will consequently contain, as nucleotide precursors, ribonucleotide triphosphates.

Other components of the amplification solution are added consequently to the choice of the nucleic acid polymerase, and they are essentially corresponding to compounds known in the art as being effective to support the activity of each polymerase. The concentration of compounds like dimethyl sulfoxide (DMSO), Bovine Serum Albumin (BSA), Triton X-100, or $MgCl_2$ is well known in the prior art as being important to have an optimal amplification, and therefore the operator can easily adjust such concentrations for the methods of the present invention on the basis of the examples presented hereafter.

The multiple copies of the nucleic acid strands making up the colonies are generally immobilized on a solid support and may be in a single, double, or mixed single-double stranded configurations, all simultaneously represented in the population of amplified molecules belonging to a single DNA colony. Therefore, if it is necessary for a method to have all the nucleic acid molecules to be analyzed and/or sequenced in specific configuration (either completely or in a segment of interest), further treatments can be applied to the isothermally amplified products to have all (or at least most) of them in such state. For example, temperature-, chemical-, or electric charge-driven denaturation can be used to transform all the amplification products into a single stranded DNA. Such molecules can now hybridize more efficiently with a primer, added in the liquid phase or attached on the support, having a sequence complementary to an internal sequence of one amplified strand. Depending on the sequencing method, this "helper" oligonucleotide can allow the detection of a sequence in different ways. It can be labeled, or it can prime the elongation using labeled/modified nucleotide(s). Alternatively, it can allow the use of an endonucleolytic enzymes recognizing a specific sequence or structure formed after the hybridization step or after the elongation step.

The nucleic acid colonies of the invention can be generated in different sizes and densities depending on the conditions used. The size of colonies is preferably from 0.2 micrometers to 6 micrometers. The density of nucleic acid colonies for use in the method of the invention is typically $1000/mm^2$ to $100000/mm^2$. Higher densities, for example $100000/mm^2$ to $10000000/mm^2$, are equally achievable by the methods of the invention. Only the technologies for image analysis (microscopes, CCD cameras, software) nowadays available put a limitation, which will be overcome probably in the future, to the clear resolution of single DNA colonies at such densities.

Once nucleic acid colonies have been generated isothermally, various technologies can be used to visualize and/or characterize simultaneously one or more of the DNA colonies, for instance, to verify that the density and the dimension of the isothermally generated DNA colonies are the ones expected. Depending from the specific technique, the output of analytical method can be obtained by monitoring either the solid support whereon the isothermal amplification was performed, or the material released from such support into the liquid phase. Optionally, nucleic acid molecules, distinct from the one(s) used for the isothermal amplification can be used for specific analytical methods and hybridized to the amplification products into the liquid phase, accordingly to the optimal hybridization conditions which can be easily determined empirically for each nucleic acid sequence using methods well known in the prior art.

Colony visualisation or the sequence determination methods which can be used on DNA colonies have been described in WO 00/18957. A non-comprehensive list of such methods comprises the hybridization with labeled oligonucleotides, the incorporation of labeled nucleotides, the re-amplification using specific probes, the use of DNA binding dyes, the digestion with sequence- or structure-specific endonucleases, and the use of other DNA modifying enzymes (such as ligases, methylases, exonucleases) and other DNA binding proteins.

The density and the dimension of the isothermally generated nucleic acid colonies can be calculated, prior to the sequence analysis, by using fluorescence detection methods, well known to the men of the art. For example, one may use an intercalating dye such, as ethidium bromide or PicoGreen™ (Molecular Probes, Eugene, Oreg.), or other chemical DNA staining method, as Ulisys™ (Molecular Probes), to stain the isothermally amplified double stranded molecules immobilized on the surface and observe the result of staining with an epifluorescence microscope, as shown in FIG. 3. Any device allowing the detection and the quantitation of the appropriate label, for example fluorescence or radioactivity, may be used for sequence determination, as summarized in WO 00/18957. Alternatives to a microscope are well know to the man of art, for example a scanning device.

The full or partial sequences of one or more nucleic acid(s) can be determined by determining the full or partial sequence of the amplified nucleic acid templates present in more than one DNA colony. Such additional step(s) can be performed on the amplified nucleic acids either on the solid support itself, or after releasing one or both nucleic acid strands belonging to one or more of the DNA colonies. Preferably a plurality of sequences is determined simultaneously.

In particular, whenever direct labeling of the amplification product, or sequencing of the amplification product, is desired, a labeled nucleotide can be introduced into the amplification solution after that the reaction proceeded enough to detect isolated DNA colonies. The labeling group can be radioactive or fluorescent, like Texas Red, and it can be added to the amplification solution, eventually together with a primer different from the ones used to amplify the template molecules, in an appropriate concentration (typically, one tenth to one thousands of the concentration of the non-labeled dATP). However, high concentrations of labeled nucleotides may inhibit the amplification process, a phenomena well known to the man of the art for other amplification techniques such as liquid phase PCR.

Therefore, the methods of the invention comprise the additional step of performing at least one step of sequence determination, of one or more of the isothermally amplified DNA colonies. The sequence determination can be consequent to the incorporation of labeled nucleotide(s), making use of the colony primers or of other primers, immobilized on the solid support or in the liquid phase. Alternatively, the sequence determination can be consequent to the hybridization with labeled oligonucleotide(s), or to the release of one or both nucleic acid strands belonging to one or more of the nucleic acid colonies.

In a further aspect of the invention, the method comprises the additional step of releasing one or both nucleic acid strands belonging to one or more of the DNA colonies generated isothermally, so that they can be recovered in solution for further use. The release of such nucleic acid can be obtained with chemical, optical, physical or enzymatic means that cleave the link between the primers and the surface, or a specific sequence, structure, or nucleotide contained in the amplified nucleic acids. For example, WO 00/58329 (Goldsborough A) provides a method of detaching a nucleic acid molecule from a solid support by cleaving selectively an unconventional nucleotide. Alternatively, sequences contained in the immobilized DNA colonies can be reamplified in the liquid phase in which the colonies are immersed by using any of the known amplification methods, like PCR.

Any DNA colony detection system is preferably used in combination with an analysis system in order to determine the number and nature of the nucleotides incorporated at each colony immediately, for example, after each step of primer extension, or later using recorded data, allowing the sequence of the nucleic acid template within a given colony to be determined.

The methods of the invention can be used to generate nucleic acid colonies in isothermal conditions. A nucleic acid colony of the invention may be generated from a single immobilized nucleic acid template of the invention. The method of the invention allows the simultaneous production of a number of such nucleic acid colonies, each of them potentially containing different immobilized sequences.

The present application provides an alternative solution to the problem of speeding up nucleic acid amplification and sequencing by providing means to significantly simplify the procedures necessary for the isothermal amplification of nucleic acids on a solid support. The present invention, even if it is applicable to nucleic acid sequences having limited lengths (up to 1000 bases), can satisfy many of the growing needs of high throughput methods.

Often, in field of genomics and related studies (pharmacogenomics, drug discovery, food characterization, genotyping, diagnostics, gene expression monitoring, genetic diversity profiling, whole genome sequencing and polymorphism discovery), the nucleic acid sequences to be determined and compared are related to several hundreds different genomic, recombinant, or retrotranscribed DNA fragments, each of them not longer than 1000 bases. Therefore, the methods of the invention are particularly useful in, but not limited to, the identification of DNA sequences in situations where many genes or mRNAs (e.g. 500) from many individuals (e.g. 500) have to be sequenced simultaneously, or the simultaneous scoring of large numbers (e.g. millions) of polymorphisms, or the monitoring of the expression of a large number of genes (e.g. 100,000) simultaneously.

For example, various methods of comprehensive gene expression analysis allow the characterization of the gene expression typical of cell subpopulations or microanatomic structures. These highly sensitive techniques make often use of complementary DNA which is fragmented in short segment of 10-20 base pairs ("tags"), a number of basis which is sufficient to identify a single mRNA species, so that the amount of mRNA encoding for a protein can be roughly calculated, or compared amongst samples, by counting the number of "tags" present in the sample associated to such mRNA. These segments are usually tandemly ligated in order to be sequenced like in the case of SAGE (Serial Analysis of Gene Expression; Velculescu V E et al., Trends Genet 2000; 16(10): 423-5) or other systems always based on the generation of tags using type IIs restriction endonucleases (WO 00/53806). The methods of the invention can facilitate the identification and the counting of the number tags. After ligating appropriate linkers sequences to each tag to allow the immobilization and isothermal amplification on a solid surface, single DNA colonies corresponding to given tag can be visualized, sequenced directly or indirectly, and scored using an image analysis software. In this way, the frequency of each tag in the cDNA population can be calculated without ligating all the tags in concatenamers to be cloned into plasmids.

A similar approach can be applied on ESTs or genomic DNA in order to identify haplotypes, or specific SNPs, associated a disease or to other phenotypes, since, also in this case, it is fundamental to identify quickly the sequence of thousand of small single nucleic acids segments.

Thus, a further aspect of the invention is the use of the isothermal nucleic acids amplification method on a solid support for providing nucleic acid molecules to be used for nucleic acid sequencing and re-sequencing in the fields of genomics, pharmacogenomics, drug discovery, food characterization, genotyping, diagnostics, gene expression monitoring, genetic diversity profiling, whole genome sequencing and polymorphism discovery, or any other applications involving the amplification of nucleic acids.

A yet further aspect of the invention provides a kit for the isothermal nucleic acids amplification on a solid support for providing nucleic acid molecules to be used for nucleic acid sequencing and re-sequencing in the fields of genomics, pharmacogenomics, drug discovery, food characterization, genotyping, diagnostics, gene expression monitoring, genetic diversity profiling, whole genome sequencing and polymorphism discovery, or any other applications involving the amplification of nucleic acids.

An example of procedure for identifying and characterizing amplification products obtained by the methods of the present invention and based on labeled nucleotides could be:

1a) generating and visualizing amplified nucleic acids onto the solid surface using methods previously described in the present patent application and recording the result;

1b) treating the amplified nucleic acids such as to remove the intercalating dye used for the visualization;

1c) transforming, at least partially, the amplified nucleic acids into single stranded molecules;

1d) providing oligonucleotide(s) in the liquid or in the solid phase, where the phase and/or the oligonucleotide(s) can be the same used into the isothermal amplification or different one(s), and where the oligonucleotide(s) should comprise a 3' end sequence capable of hybridizing with a sequence present in at least one amplified product;

1e) providing the conditions for the hybridization between the oligonucleotide(s) and the amplified molecule;

1f) providing a nucleic acid polymerase and at least one type of labeled nucleotide into the liquid phase, together with a suitable buffer, in conditions allowing primer elongation;

1g) detecting the amplified nucleic acids incorporating the labeled nucleotide(s) by the means of such label or by the means of the interaction of this label with the amplified product, and recording the result;

1h) optionally removing the liquid phase and repeating step 1f) and 1g) using nucleotide(s) having a label different from one used in the previous elongation, and recording the result; 1i) optionally repeating step 1c) to 1f) using oligonucleotides and/or labeled nucleotide(s) different from one used in the previous elongation, and recording the result.

The above procedure is particularly useful to allow the base-by-base sequencing of the amplified products of the invention, when the relative variations of the results are converted into a signal and compared to put in evidence the incorporation of a labeled nucleotide, as described in WO 00/18957.

An example of procedure for identifying and characterizing amplification products obtained by the methods of the present invention and based on labeled oligonucleotides could be:

2a) generating and visualizing amplified nucleic acids onto the solid surface using methods previously described in the present patent application and recording the result;

2b) treating the amplified nucleic acids such as to remove the intercalating dye used for the visualization;

2c) transforming, at least partially, the amplified nucleic acids into a single stranded molecules;

2d) providing oligonucleotide(s) in the liquid or in the solid phase, where the phase and/or the oligonucleotide(s) can be the same used into the isothermal amplification or different one(s), and where the oligonucleotide(s) should comprise a 3' end sequence capable of hybridizing with a sequence present in at least one amplified product;

2e) providing the conditions for the hybridization between the oligonucleotide(s) and the amplified molecules;

2f) detecting the amplified nucleic acids hybridizing with the labeled oligonucleotide (s) by the means of such label or by the means of the interaction of this label with the amplified product and recording the result;

2g) optionally repeating steps 2c) to 2f), or 2e) to 2f), using oligonucleotide(s) containing a different sequence and/or different label, and recording the result.

An example of procedure for identifying and characterizing amplification products obtained by methods of the present invention and based on restriction enzymes could be:

3a) generating and visualizing amplified nucleic acids onto the solid surface using methods previously described in the present patent application and recording the result;

3b) treating the amplified nucleic acids such as to remove the intercalating dye used for the visualization;

3c) treating the amplified nucleic acids with a solution containing at least one restriction endonuclease, potentially cutting into a two stranded nucleic acid molecule present into at least one amplification product of the invention and/or obtained after step b), together with a suitable buffer and in conditions allowing such enzymatic activity;

3d) recovering the released nucleic acids;

3e) repeating step 3a) and recording the result; comparing the results of the visualization before and after digestion;

3f) optionally repeating steps 3b) to 3e) with a different restriction endonuclease, and recording the result.

Once understood the features of the amplification methods and products disclosed in present application, the necessity and kind of such analysis-specific additional steps can be easily deduced by reviewing prior art, as well as the nonlimiting following figures and examples describing the basic details and some applications of the invention.

EXAMPLES

Example 1

Isothermal Amplification of Template DNA Immobilized on a Solid Surface

Methods

DNA Sequences

Primers P1 (24-mer; SEQ ID NO: 1), P2 (24-mer; SEQ ID NO: 2), and P3 (40-mer; SEQ ID NO: 3) are synthetic oligonucleotides carrying a C6 amino link group at their 5' extremity. This chemical group has been used to immobilize primers and templates on the solid surface to apply the methods of the invention.

The templates T3 (SEQ ID NO: 9) and T4 (SEQ ID NO: 10), which are 68-mers having a sequence corresponding to P1 at the 5' end, and a sequence complementary to P2 at the 3' end, and T90 (90-mer having a sequence corresponding to P1 at the 5' end, and a sequence complementary to P2 at the 3' end; SEQ ID NO: 11) are synthetic oligonucleotides carrying a C6 amino link group at their 5' end (T90), or 5' phosphate group (T3 and T4).

The templates T155 (155-mer; SEQ ID NO: 12), T203 (203-mer; SEQ ID NO: 13), T386 (386-mer, SEQ ID NO: 14), and T605 (605-mer; SEQ ID NO: 15) have sequences corresponding to P3 at the 5' end, and a sequence complementary to P2 at the 3' end. They have been constructed by amplifying nested fragments of T1 (SEQ ID NO: 8) a 823 base pair sequence contained in a pBSk-plasmid (Stratagene), as shown in FIG. 2. The direct primer P3 (a 40-mer having a sequence corresponding to P1 at the 5' end, and a sequence complementary to a 16 nucleotides long T1 sequence at the 3' end; SEQ ID NO: 3) carries a 5' amino link group. The reverse primers P155r (SEQ ID NO: 4), P203r (SEQ ID NO: 5), P386r (SEQ ID NO: 6), and P605r (SEQ ID NO: 7) are 44-mer synthetic oligonucleotides having a sequence corresponding to P2 at the 5' end, and a sequence complementary to different 16 nucleotides long T1 sequences). These templates were amplified using 100 microliters of a solution containing 5 Units of Taq polymerase (PerkinElmer), 1× Taq buffer (Perkin-Elmer), dNTPs (dATP, dGTP, dCTP, dTTP, Pharmacia) 200 microMolar, 5 nanograms/microliter of the pBSk-plasmid, primer P3 1 microMolar, and 1 microMolar of the corresponding reverse primer. Twenty PCR cycles (94° C. for 30 seconds, 62° C. for 30 seconds, 72° C. for 60 seconds) were performed, and the resulting product was purified using a QiaQuick kit (Qiagen) following the instruction of the manufacturer. The solution used to recover the purified nucleic acids contained sodium borate 10 milliMolar (pH 7.5).

All Synthetic Oligonucleotides were Obtained from Microsynth (Switzerland)

Protocol for the Immobilization of Primer and Template Nucleic Acid on a Solid Surface The solid surface used to demonstrate the feasibility of the methods of the invention was represented by the interior of flat bottomed wells made of a functionalized synthetic material called Nucleolink™ (Nunc, Denmark), and assembled in plates having an overall shape that fits into a 96 wells PCR machine. When filled with the volume of immobilization and amplification solution used in the examples (15-20 microliters), the surface of each well actually exposed to these solutions corresponds approximately to 30 mm$^2$.

Primers and templates were attached in Nucleolink™ plates, which were kept on ice while the nucleic acids are diluted in an immobilization solution containing Imidazole 10 nanoMolar and 1-ethyl-3-(3-dimethylaminopropyl)-carbodiimide hypochloride (EDC) 10 milliMolar, and added to the wells. Once that all the wells were filled, the plates were incubated for 10 minutes at 50° C. The wells were then washed at room temperature two times with a solution containing NaOH 0.4 Molar and Tween-20 0.1%, and finally three times with TNT, a solution containing Tris-HCl 100 milliMolar (pH 7.5), NaCl 150 milliMolar, Tween-20 0.1%, before being submitted to the isothermal amplification.

Protocol for the Visualization of the Amplified Nucleic Acids

After the isothermal amplification, the wells were rinsed three times in Tris-HCl 20 milliMolar (pH 7.5), and then the DNA colonies were visualized by incubating the wells with PicoGreen™ (Molecular Probes), a molecule which is fluorescent when bound to double-stranded DNA, routinely diluted 2000 fold in Tris-HCl 20 milliMolar (pH 7.5). Each well was incubated with 50 microliters of the PicoGreen™ dilution for 10 minutes at room temperature.

The DNA colonies immobilized on the bottom of the wells were observed using an epifluorescence microscope (Axiovert 100TV, Zeiss, Germany) equipped with a cooled CCD camera (Micomax 512×768, Princeton instruments, Trenton, N.J.) which is controlled by the Winview software (Princeton instruments, Trenton, N.J.). The images were obtained after an exposure time of 2 seconds and analyzed using the analysis software (Soft Imaging System GmBH, Germany) or other equivalent software.

Results

The primers P1 and P2 and the nucleic acid templates T90 and T386 were attached on Nucleolink™ wells as described before. The templates contain a number of nucleotides approximately 0.6 and 2.5 times the persistence length to identify a first range of template length at which the methods of the invention are applicable.

The wells were filled with 20 microliters of immobilization solution containing the primers P1 and P2 (each 250 nanoMolar), and template type and concentration different for each well, as indicated in Table I:

TABLE I

| Well Number | Template name | Template concentration (nanoMolar) |
|---|---|---|
| A1 | T90 | 3.1 |
| B1 | T90 | 1 |
| C1 | T90 | 0.3 |
| D1 | T90 | 0.1 |
| E1 | T90 | 0.03 |
| F1 | T90 | 0.01 |
| G1 | T90 | 0.003 |
| H1 | — | 0 |
| A2 | T386 | 3.1 |
| B2 | T386 | 1 |
| C2 | T386 | 0.3 |
| D2 | T386 | 0.1 |
| E2 | T386 | 0.03 |
| F2 | T386 | 0.01 |
| G2 | T386 | 0.003 |
| H2 | — | 0 |

The isothermal amplification was performed by incubating the wells 1 hour at 78° C. with 15 microliters of an amplification solution containing 1 Unit of Pfu Polymerase (Stratagene), 10% Dimethyl Sulfoxide (DMSO), dNTP (dATP, dGTP, dCTP, dTTP, Pharmacia) 80 microMolar, Tris-HCl (pH 8.8) 200 milliMolar, KCl 10 milliMolar, $(NH_4)_2SO_4$ 10 milliMolar, $MgSO_4$ 2 milliMolar, Triton X-100 0.1%, and 0.1 mg/ml BSA. The isothermal incubation was performed using a standard 96-wells PCR machine (MJ-Research PTC-200) set constantly at 78° C. using the heated lid.

The resulting images are shown in FIG. 3. Due to the DNA staining procedure used, the signal is due to the presence of (at least partly) double stranded DNA amplified and immobilized into colonies onto the bottom of the Nucleolink™ wells. The images have been inverted for a better printout. Signal smaller or equal to 130 AU (Arbitrary Units, as calculated by the software controlling the CCD camera) appears white and signal higher or equal to 350 AU appears black.

FIG. 3 shows that, when primers only have been attached (H1 and H2), the image is totally white, demonstrating that there is no detectable spontaneous amplification. While at the highest concentrations of template (A1/2, B1/2), the amplification products cover the whole surface saturating the image, distinct DNA colonies have been obtained in wells C1/2, D1/2, and E1/2, at sub nanoMolar concentrations of both templates. The number of such "spots" (each occupying an area of 1 to 5 square micrometers) grows approximately linearly with the concentration of template used during the attachment step. The amplification has been performed with templates having two different lengths and using different template/primer ratios during the immobilization procedure.

Figure 4:
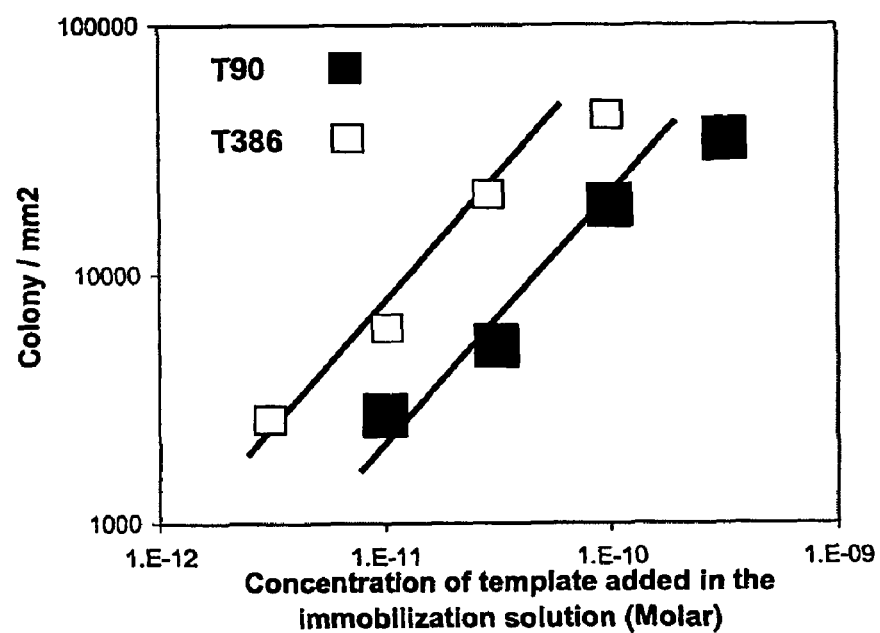
FIG. 4: log-log plot of the density of DNA colony observed at the bottom of PicoGreen™ stained wells after isothermal amplification when different concentrations of template have been immobilized. Each point is an average of 3 observations. The slope of the line is one.

A more quantitative analysis of the isothermal amplification effectiveness in terms of number of DNA colonies is presented in FIG. 4. In the tested experimental conditions (Imidazole/EDC nucleic acid immobilization solution, Nucleolink™ wells, 10 minutes of incubation at 50° C., and two primers 250 milliMolar each), templates in the range of 90-386 nucleotides, added into the immobilization solution at sub nanoMolar concentrations, can be amplified isothermally as DNA colonies on a solid surface, obtaining several tens of thousands of DNA colonies per square millimeter.

The isothermal amplification procedure was applied also using other template lengths and different concentration of primers. Series of eight Nucleolink™ wells were filled with 20 microliter of immobilizing solution containing a constant sub-nanoMolar concentration of one template for the series A (T155 0.14 nanoMolar), B (T203 0.2 nanoMolar), C (T386, 0.08 nanoMolar), and D (T606 0.04 nanoMolar). The concentrations have been defined on the basis of curves obtained for each template, as shown in FIG. 4 for two of them.

The eight wells contained P1 and P2 at the concentrations shown in Table II.

TABLE II

| Well Number | P1 (nanoMolar) | P2 (nanoMolar) |
|---|---|---|
| 1 | 250.0 | 250.0 |
| 2 | 75.0 | 75.0 |
| 3 | 55.0 | 55.0 |
| 4 | 37.5 | 37.5 |
| 5 | 22.5 | 22.5 |
| 6 | 6.8 | 6.8 |
| 7 | 2.0 | 2.0 |
| 8 | 0.6 | 0.6 |

Figure 5:
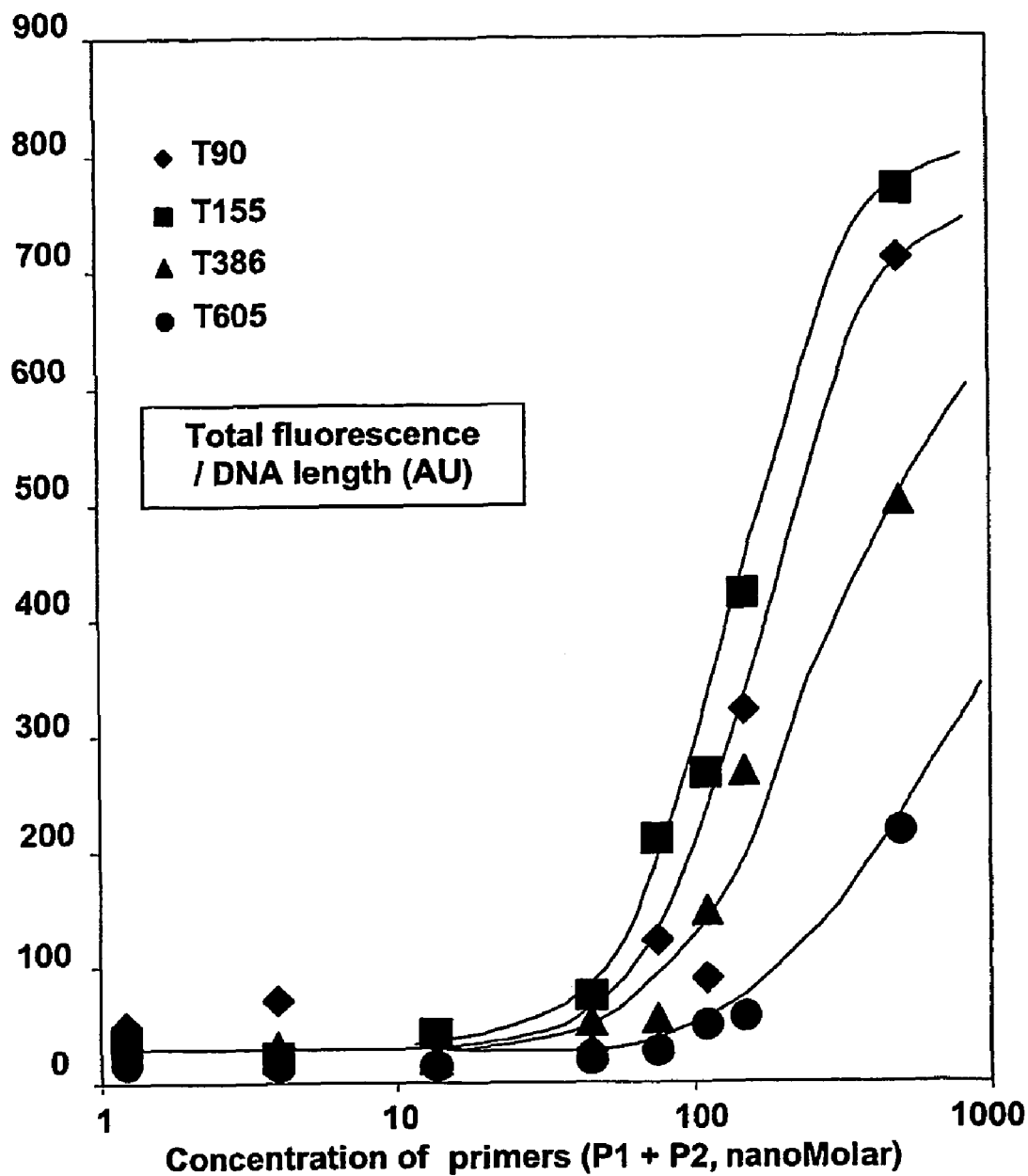
FIG. 5: variation of total fluorescence obtained when templates of different length are amplified isothermally. The same arbitrary unit is used for all the curves.

After performing the isothermal amplification as described before, the effectiveness of the method of the invention has been measured in terms of fluorescence signal, normalized for the template length, at different primer concentrations (FIG. 5). The normalization is necessary since longer templates incorporate more DNA staining compound, so that the raw fluorescence signal, after subtracting the background, was divided by the length of the template (expressed in kilobases).

This experiments shows that the amount of primers P1 and P2, necessary to obtain detectable level of amplification following the method of the invention in the immobilization and amplification conditions set previously, partially depends on the template length. While the signal is strong enough when the total primers concentration is less than 100 nanoMolar for smaller templates having a length approximating the persistence length (T90 and T155, respectively 0.6 and 1 time the persistence length), longer templates (T386 and T605, respectively 2.5 and 4 times the persistence length) are still amplified but need a total primers concentration superior to 100 nanoMolar. These results suggest that less mechanical stress is inducible in longer immobilized nucleic acids, which probably can assume alternative tridimensional configuration absorbing a fraction of the mechanical stress necessary to drive the isothermal strand separation and displacement.

In order to verify that the amplified products are truly obtained by appropriately immobilizing primers and templates onto the solid surface, the following control experiments were performed.

Figure 6:
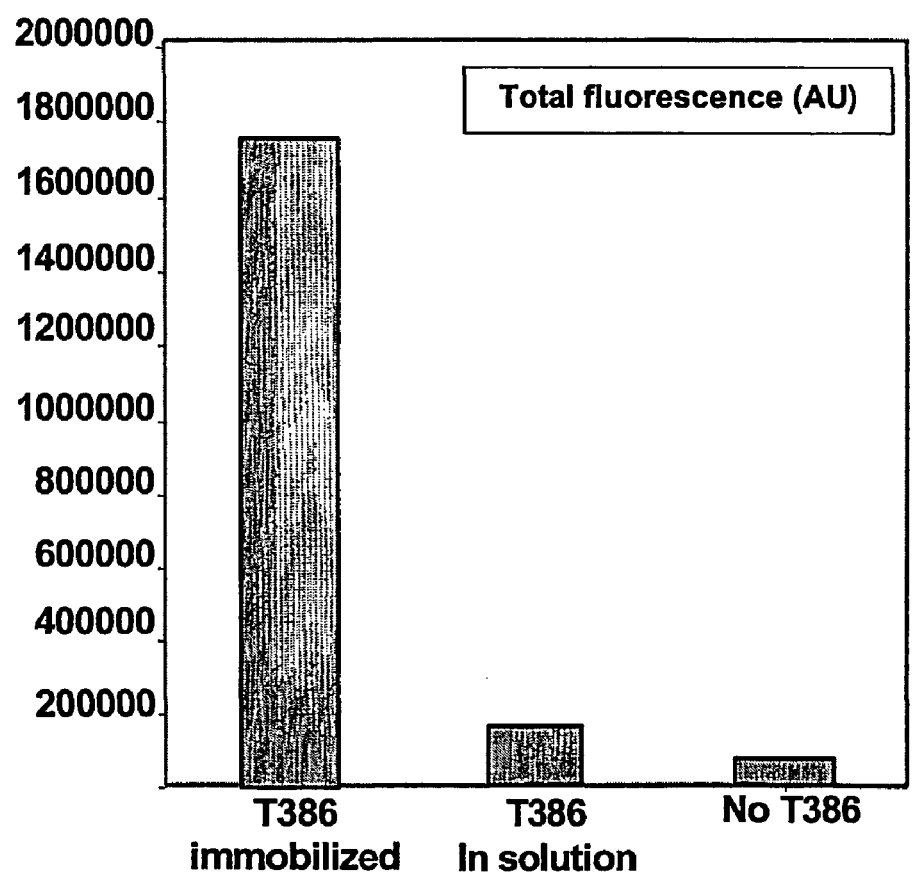
FIG. 6: comparison of the total fluorescence obtained when the template T386 is immobilized onto the wells or in solution, or the template T386 is absent from the amplification process.

In a first experiment, the isothermal amplification and visualization protocol previously described was performed with or without immobilized primers (P1 and P2, 250 milliMolar each), and with a template (T386, 0.08 nanoMolar), either immobilized or in solution. As shown in FIG. 6, the total fluorescence is very weak when the template is either in solution or absent, even if large amounts of primers are immobilized. Such signal is probably due to marginal self-amplification. It is anyway evident that only the immobilization of both primers and template enables the isothermal amplification of double stranded DNA in the form of DNA colonies.

In a second control experiment, the same nucleic acids used in the previous experiments were used in liquid phase using PCR conditions or the same isothermal conditions applied on the solid surface.

The amplification solution used for the amplification experiments contained 0.05 Unit/microliter of Pfu Polymerase (Stratagene), dNTP (dATP, dGTP, dCTP, dTTP, Pharmacia) 80 microMolar, Tris-HCl (pH 8.8) 200 milliMolar, KCl 10 milliMolar, $(NH_4)_2SO_4$ 10 milliMolar, $MgSO_4$ 2 milliMolar, Triton X-100 0.1%, 0.1 mg/ml BSA, primer P1 1 microMolar, primer P2 1 microMolar, without or with the template (T386 0.13 nanoMolar, or T90 0.33 nanoMolar). The amplification solution was divided in three aliquots, each submitted to a different amplification condition: 20 cycles of thermocycling PCR (94° C. for 30 seconds, 60° C. for 30 seconds, 72° C. for 1 minute), 1 hour at 72° C., or 1 hour at 78° C. The amplification products were purified on Qiaquick Columns (Qiagen) and loaded on a 2% agarose gel.

Figure 7:
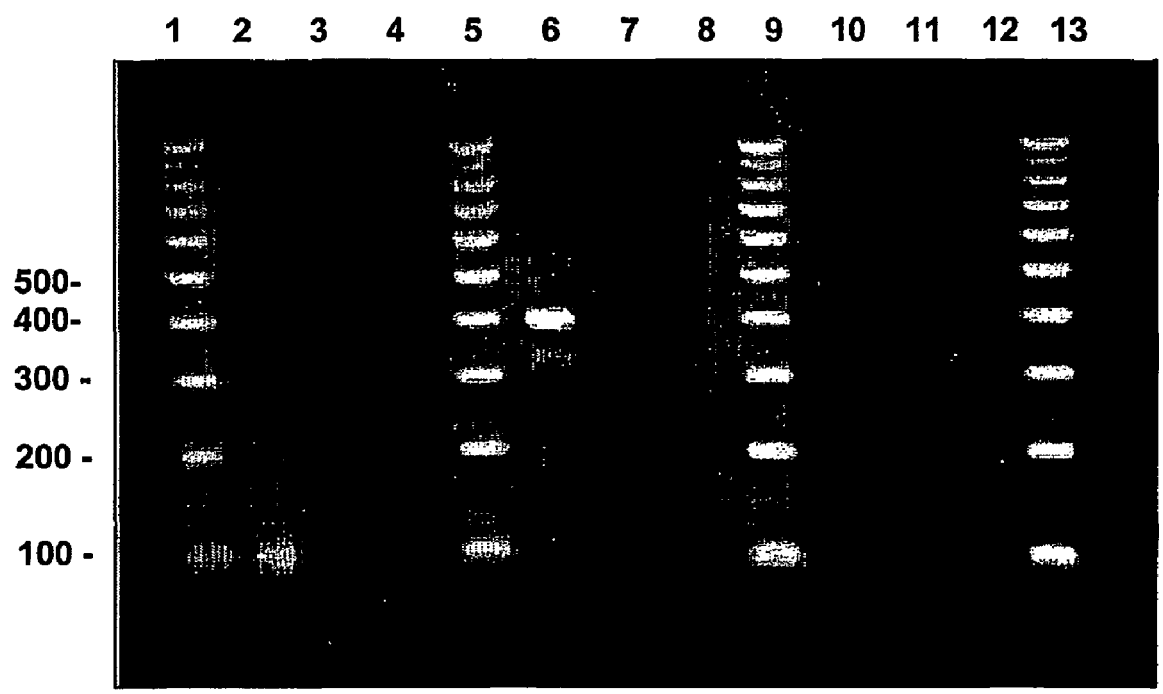
FIG. 7: digitalized image of a 2% agarose gel loaded with the amplification products obtained by PCR or by liquid isothermal amplification, which has been run 30 minutes at an electric field of 10V/cm. Lane 1, 5, 9, 13: 2.5 microliters of Molecular weights markers (Superladder low, 100 base pair ladder; Gensura), with relevant base numbers indicated on the left. Lane 2, 3 and 4: 6 microliters of amplified and purified template T90 generated after thermocycling PCR (lane 2), or in isothermal conditions at 72° C. (lane 3) and 78° C. (lane 4). Lane 6, 7 and 8: 2.5 microliters of amplified and purified template T386 generated after thermocycling PCR (lane 6), or in isothermal conditions at 72° C. (lane 7) and 78° C. (lane 8). Lane 10, 11 and 12: 2.5 microliters of amplified and purified negative control (primers only) generated after thermocycling PCR (lane 10), or in isothermal conditions at 72° C. (lane 11) and 78° C. (lane 12). The gel has been stained with SybrGreen™ (Molecular Probes, Eugene Oreg.).

As shown in FIG. 7, no amplification products were obtained in isothermal conditions, even though the primers can amplify the same template in liquid when thermocycling conditions are applied.

The efficiency of different commercial DNA polymerases for applying the methods of the invention was tested by measuring the incorporation of a radioactive nucleotide. The isothermal amplification was performed using P1 and P2 as primers (250 nanoMolar each), with or without T3 and T4, very short templates (68-mer) added in large excess (5 nanoMolar each). The isothermal amplification was performed at 80° C. for 90 minutes using 20 microliters of an amplification solution containing 0.5 Unit DNA Polymerase, 5% DMSO dNTP (dATP, dGTP, dCTP, dTTP, Pharmacia) 80 microMolar, Tris-HCl (pH 8.8) 200 milliMolar, KCl 10 milliMolar, $(NH_4)_2SO_4$ 10 milliMolar, $MgSO_4$ 2 milliMolar, Triton X-100 0.1%, 0.1 mg/ml BSA, and $\alpha^{32}$P-dCTP 0.128 microMolar. The DNA polymerase used were Dynazyme™ (Finzyme, Finland), Pfu polymerase (Promega), Taq polymerase (Perkin Elmer), and Vent™ polymerase (New England Biolabs).

After the isothermal amplification, the Nucleolink™ wells were rinsed five times in Tris-HCl (pH 7.5) 20 milliMolar, placed into scintillation fluid (Ultima gold; Packard), and counted on a Beckmann scintillation counter to calculate the amount of labeled nucleotide incorporated.

Figure 8:
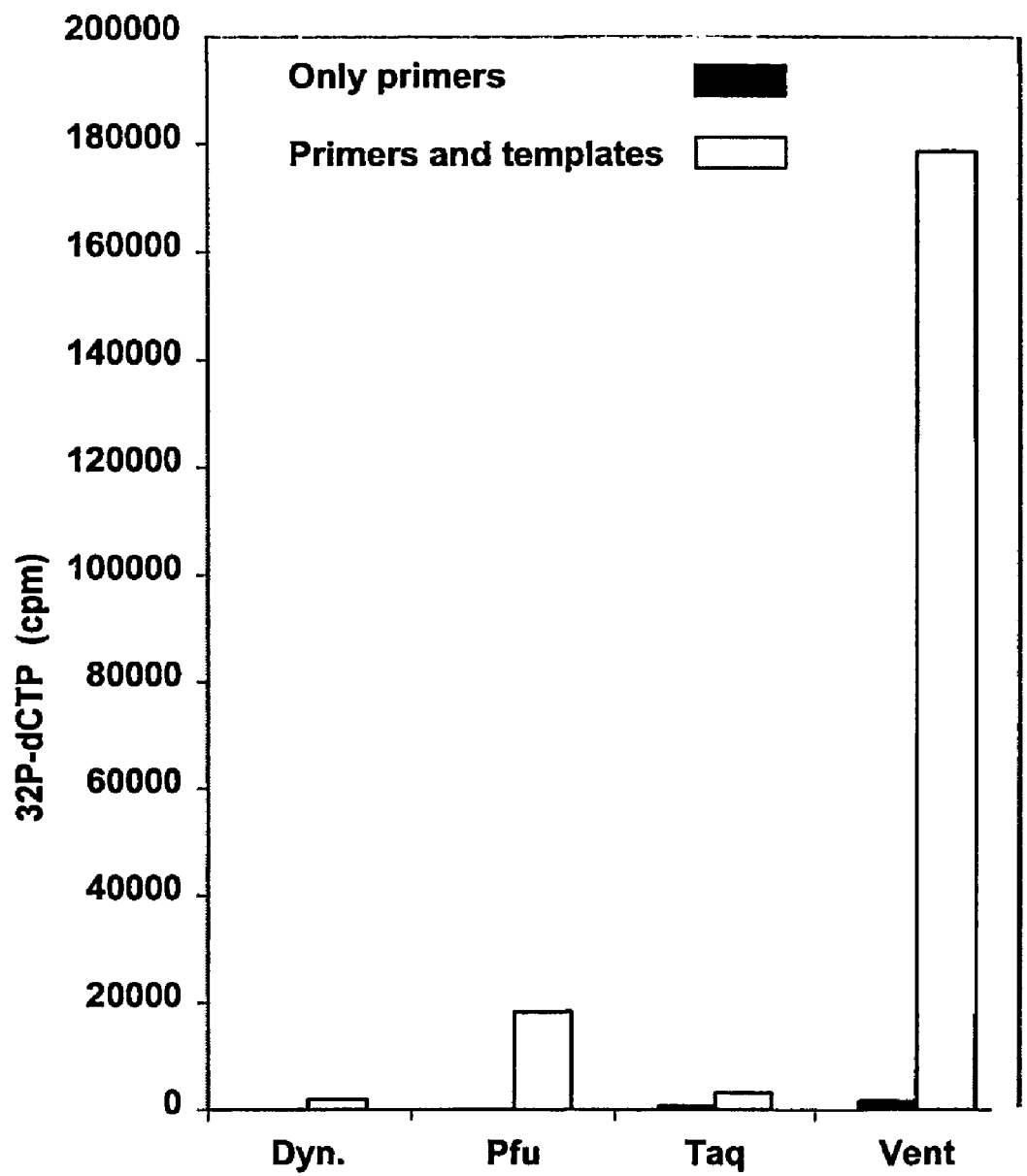
FIG. 8: average of 2 counting experiments showing the amount of $^{32}$P-dCTP incorporated using isothermal amplification using different enzymes: Dynazyme (Dyn.), Pfu polymerase (Pfu), Taq polymerase (Taq), Vent™ (Vent).

As shown in FIG. 8, all the tested polymerases allow the isothermal amplification by the methods of the invention, but with different yields and different background amplification levels. Pfu and Vent™ polymerases have the best ratio of specific over unspecific signal.

Other alternative conditions for applying the isothermal amplification of the invention were tested regarding the temperature and the concentration of DMSO, comparing the results obtained using the templates of different length.

Each template (T155 0.14 nanoMolar, T203 0.2 nanoMolar, T386 0.08 nanoMolar, and T606 0.04 nanoMolar) was immobilized in distinct series of Nucleolink™ wells together with the primers P1 and P2, 250 nanoMolar each. The isothermal amplification was then performed either using 10% DMSO but in a PCR machine creating a temperature gradient along the series of wells, or at 78° C. but in presence of various DMSO amounts After the isothermal amplification, rinsing, and visualization, the total fluorescence of DNA colonies was measured with an image analysis software quantifying the intensity of all the spots present on the image. As shown in FIGS. 9A and 9B, the amount of amplified product can highly depends on the applied amplification conditions. The isothermal amplification is particularly efficient, for all templates, at temperatures between 77 and 81° C., and at DMSO concentrations between 8% and 14%.

Example 2

Analysis of the Amplified Nucleic Acid

Once that the DNA colonies were obtained isothermally, some experiments were performed to evaluate some features of the amplified nucleic acids.

The average amount of nucleic acid strands present in each spot was estimated using both DNA staining and radiolabeled nucleotides, using Pfu polymerase and the conditions for immobilization, amplification, visualization and counting used for the experiment represented in FIG. 8.

The template T386 was added in series of wells at different concentrations (1 nanoMolar, 0.31 nanoMolar) or was absent. The counts were converted to number of molecules per DNA colony considering the surface of the well covered by the volume of amplification solution (approximately 27.56 $mm^2$ when using a volume of 15 microliters and a well having a diameter of 4 millimeters), the size of each image analyzed (approximately 0.08 $mm^2$), as well as the label specific activity. The results are summarized in Table III

TABLE III

|  | Wells containing T386 1 nanoMolar | | | | | | Wells containing T386 0.3 nanoMolar | | | | | | No T386 |
|---|---|---|---|---|---|---|---|---|---|---|---|---|---|
| Counts | 8304 | 8536 | 6754 | 8615 | 6427 | 4867 | 3687 | 4787 | 4988 | 2902 | 3693 | 4072 | 843 |
| Colonies N° | 3846 | 3831 | 3149 | 3788 | 2844 | 2349 | 1808 | 2087 | 2408 | 1218 | 1638 | 1935 | 0 |
| Average strands N° per colony | 3007 | 3103 | 2987 | 3167 | 3147 | 2885 | 2840 | 3194 | 2885 | 3318 | 3140 | 2931 | N.A. |
|  | 3049 +/−109 | | | | | | 3051 +/−193 | | | | | | |

N.A.: not applicable

This experiment shows that the methods of the invention allow to amplify isothermally a single template molecule to several thousand of strands immobilized in a discrete area. Moreover, while the number of DNA colonies is clearly dependent from the concentration of template, the efficiency of the method of the invention, measured as number of amplified strands per DNA colony, is independent from the concentration of the template in working conditions (i.e. in the nanoMolar range).

Figure 10:
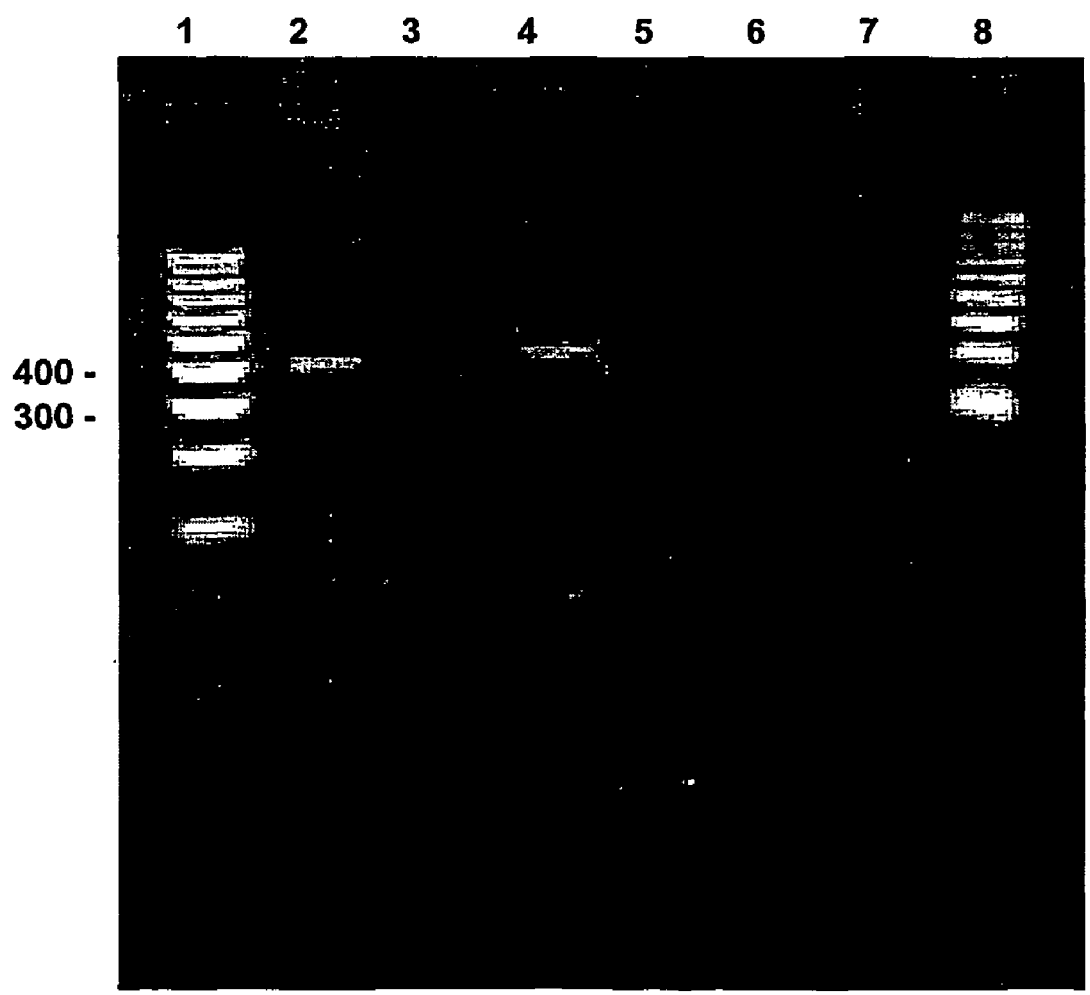
FIG. 10: digitalized image of an agarose gel which has been run 30 minutes at an electric field of 10V/cm and which has been loaded with the PCR products obtained using different starting materials. Lane 1 and 8 is a 100 bp DNA ladder (Superladder low, Gensura), with relevant base numbers indicated on the left. The PCR starting material was 0.1 nanograms of T386 (lane 2), no starting material (lane 3), an aliquot of the wells where T386 was (lane 4 and 6) or not (lanes 5 and 7) immobilized, and the isothermal amplification was (lane 4 and 5) or not (lanes 6 and 7) previously performed. The gel has been stained with SybrGreen™ (Molecular Probes, Eugene Oreg.). The faint bands at the bottom of the gel are the primers used for PCR amplification.

It was also possible to recover the products of the isothermal amplification from the surface. The immobilization protocol described before was applied in four wells, using P1 and P2 in all of them and T386 only in two of them, but only two, one with and one without T386 immobilized, were submitted to the isothermal amplification protocol as described before. All the wells were than filled with a 60 microliters of a PCR solution containing 5 Units of Pfu Polymerase (Stratagene), 10% DMSO, dNTP (dATP, dGTP, dCTP, dTTP, Pharmacia) 100 microMolar, Tris-HCl (pH 8.8) 200 milliMolar, KCl 10 milliMolar, $(NH_4)_2SO_4$ 10 milliMolar, $MgSO_4$ 2 milliMolar, Triton X-100 0.1%, 0.1 mg/ml BSA, and primers P3 and P386r (1 microMolar each). One PCR cycle is performed in the wells (94° C. for 30 seconds, 60° C. for 30 seconds, 72° C. for 60 seconds), and then 30 microliters of the PCR solution were transferred into a PCR tube. As a control, another PCR tube was filled with 30 microliters of the same PCR solution to which 0.1 nanogram of T386 were added. Ten PCR cycles (94° C. for 30 seconds, 60° C. for 30 seconds, 72° C. for 60 seconds) was then performed and 4 microliters of each sample were loaded on a 2% agarose gel. The result is given in FIG. 10. The isothermal amplification product gives a PCR product comparable to the PCR product obtained when T386 is present in solution, while the product is barely visible if the DNA attached to a tube that has not undergone isothermal amplification. The controls show that no artifact, such as primer-dimers, are arising neither during isothermal amplification nor during PCR amplification.

The invention claimed is:

1. A method for isothermally amplifying single stranded nucleic acid molecules immobilized on a solid support comprising:
  i) providing a plurality of different nucleic acid template molecules and attaching a sequence Y to a 5' end of each of the nucleic acid template molecules and a sequence Z to a 3' end of each of the nucleic acid template molecules to generate different nucleic acid template molecules comprising the same sequence Y at the 5' end and the same sequence Z at the 3' end;
  ii) providing a solid surface comprising a plurality of first primers comprising sequence X immobilized at their 5' ends and a plurality of second primers comprising sequence Y immobilized at their 5' ends, wherein sequence X is hybridizable to sequence Z;
  iii) contacting the nucleic acid template molecules comprising sequence Y at the 5' end and sequence Z at the 3' end with the solid surface to generate at least one 5'-end immobilized first single stranded nucleic acid template molecule comprising the sequence Y at the 5' end and the sequence Z at the 3' end;
  iv) annealing said at least one 5'-end immobilized first single stranded nucleic acid template molecule to said first immobilized primers, wherein sequence Z of each template molecule is annealed to one of said first immobilized primers comprising sequence X;
  v) performing a primer extension reaction using said first immobilized primers that are annealed to said 5'-end immobilized first single stranded nucleic acid template molecules to generate double stranded nucleic acid molecules comprising 5'-end immobilized first and second single stranded nucleic acid molecules, wherein the 5'-end immobilized second single stranded nucleic acid molecules are complementary copies of the 5'-end immobilized first single stranded template nucleic acid molecules and each of the 5'-end immobilized second single stranded nucleic acid molecules comprises a sequence at the 3' end that is hybridizable to the second primer sequence Y;
  vi) denaturing said double stranded nucleic acid molecules to generate 5'-end immobilized first and second single stranded nucleic acid molecules;
  vii) annealing said 5'-end immobilized first and second single stranded nucleic acid molecules to said first immobilized primers comprising sequence X and said second immobilized primers comprising sequence Y, respectively;
  viii) performing a primer extension reaction using primer annealed 5'-end immobilized first and second single stranded nucleic acid molecules as templates to generate double stranded nucleic acid molecules immobilized at both 5'-ends;
  ix) repeating steps vi through viii to generate DNA colonies, wherein each DNA colony comprises multiple copies of the 5'-end immobilized first and second single stranded nucleic acid molecules on said solid surface, wherein steps vi through viii are carried out at the same temperature.

2. The method as claimed in claim 1, wherein the first and second primers are mixed with the nucleic acid templates prior to immobilization, wherein first primers comprising sequence X can hybridize the sequence Z of the nucleic acid templates and second primers comprise a sequence identical to the sequence Y of the nucleic acid templates.

3. The method as claimed in claim 1 or 2, wherein said nucleic acid template molecules are genomic DNA, complementary DNA, or recombinant DNA.

4. The method as claimed in claim 3, wherein the nucleic acid template molecules contain between 68 and 605 bases.

5. The method as claimed in claim 4, wherein the nucleic acid template molecules in the immobilization solution have a concentration between 1 nanoMolar and 0.01 nanoMolar.

6. The method as claimed in claim 1 or 2, wherein said nucleic acid template molecules are natural, synthetic, or modified nucleic acid molecules and wherein the nucleic acid molecule is DNA, RNA, or mRNA.

7. The method as claimed in claim 1 or 2, wherein the first and second primers in the immobilization solution have a concentration comprised between 1000 and 50 nanoMolar.

8. The method as claimed in claim 1 or 2, wherein each of said primer extension reactions is performed by a nucleic acid polymerase, wherein said nucleic acid polymerase is a DNA-dependent DNA polymerase or an RNA-dependent DNA polymerase.

9. The method as claimed in claim 8, wherein said nucleic acid polymerase is a DNA polymerase which is active between 70° C. and 85° C.

10. The method as claimed in claim 9, wherein each of said primer extension reactions is performed at a temperature comprised between 77° C. and 81° C.

11. The method as claimed in claim 1 or 2, wherein the 5' ends of both the nucleic acid template molecules and the first and second primers are immobilized via chemically modifiable functional groups which allow formation of covalent binding between said nucleic acid template molecules or said first and second primers and a solid support.

12. The method as claimed in claim 11, wherein the nucleic acid template molecules and first and second primers are modified with thiol, phosphate or an amino group at the 5' end and immobilized using an immobilization solution containing 1-ethyl-3-(3-dimethylaminopropyl)-carbodiimide hydrochloride (EDC).

13. The method as claimed in claim 1 or 2, wherein each of the primer extension reactions is performed in a solution comprising dimethyl sulfoxide (DMSO).

14. The method as claimed in claim 1, wherein the density of nucleic acid colonies generated is between 1000 and 100000 per $mm^2$.

15. The method as claimed in claim 1, comprising an additional step of visualizing the nucleic acid colonies.

16. The method as claimed in claim 15, wherein double stranded DNA intercalating agent, labeled nucleotide(s), or labeled oligonucleotide(s) are used to visualize the nucleic acid colonies.

17. The method as claimed in claim 1, comprising an additional step of releasing one or more immobilized nucleic acid strands belonging to one or more of the nucleic acid colonies with chemical, optical, physical or enzymatic means.

18. The method as claimed in claim 1, comprising an additional step of performing at least one step of sequence determination of one or more of the nucleic acid colonies.

19. The method as claimed in claim 18 wherein the sequence determination is obtained by incorporating labeled nucleotide(s).

20. The method as claimed in claim 18, said method comprising an additional step of releasing one or more immobilized nucleic acid strands belonging to one or more of the nucleic acid colonies with chemical, optical, physical or enzymatic means, wherein the sequence determination is subsequent to the release of one or both nucleic acid strands.

21. The method as claimed in claim 18, wherein full or partial sequences of the amplified nucleic acids present in at least one of the nucleic acid colonies are determined.

22. The method as claimed in claim 18 wherein the sequence determination is achieved by hybridization with labeled oligonucleotide(s) to the nucleic acid strands belonging to one or more of the nucleic acid colonies.

23. The method as claimed in claim 19 or 22, wherein the labeled nucleotides or labeled oligonucleotides comprise a label that is a radioactive or a fluorescent group.

24. The method as claimed in claim 19 wherein the labeled nucleotide(s) are incorporated by extending one of the immobilized primers.

25. The method as claimed in claim 19 wherein the labeled nucleotide(s) are incorporated by extending non-immobilized primers hybridized to the amplified nucleic acids of nucleic acid colonies.

26. A method for amplifying nucleic acid molecules comprising:
(a) providing a plurality of different nucleic acid molecules each comprising a different nucleic acid template sequence, the same sequence Y at the 5' end of the template sequence and the same sequence Z at the 3' end of the template sequence;
(b) providing a solid surface comprising two different colony primers X' and X", wherein the colony primers X' comprise a sequence complementary to the sequence Z and colony primers X" comprises a sequence that is the same as the sequence Y;
(c) immobilizing the different nucleic acid molecules to the solid surface; and
(d) amplifying to extend the two different colony primers X' and X" immobilized on the solid surface, wherein the amplifying is carried out isothermally, thereby forming multiple double stranded copies of each of the different nucleic acid template sequences that are immobilized to the surface at both 5' ends.

27. The method of claim 26, wherein step (d) comprises
i) performing a primer extension reaction using colony primers X' to generate double stranded nucleic acid molecules comprising 5'-end immobilized first and second single stranded nucleic acid molecules, wherein the 5'-end immobilized second single stranded nucleic acid molecules are complementary copies of the 5'-end immobilized first single stranded template nucleic acid molecules and each of the 5'-end immobilized second single stranded nucleic acid molecules comprises a sequence at the 3' end that is hybridizable to colony primers X";
ii) denaturing the double stranded nucleic acid molecules to generate 5'-end immobilized first and second single stranded nucleic acid molecules;
iii) annealing the 5'-end immobilized first and second single stranded nucleic acid molecules to the two different colony primers X' and X";
iv) performing a primer extension reaction using primer annealed 5'-end immobilized first and second single stranded nucleic acid molecules as templates to generate double stranded nucleic acid molecules immobilized at both 5'-ends; and
v) repeating steps ii) through iv) to generate DNA colonies, wherein each DNA colony comprises multiple copies of the 5'-end immobilized first and second single stranded nucleic acid molecules on the solid surface, wherein steps i) through iv) are carried out at the same temperature.

* * * * *

UNITED STATES PATENT AND TRADEMARK OFFICE
CERTIFICATE OF CORRECTION

| | | |
|---|---|---|
| PATENT NO. | : 7,790,418 B2 | |
| APPLICATION NO. | : 10/433965 | |
| DATED | : September 7, 2010 | |
| INVENTOR(S) | : Pascal Mayer | |

It is certified that error appears in the above-identified patent and that said Letters Patent is hereby corrected as shown below:

Column 32, in claim 2, line 55, after hybridize insert --to--.

Signed and Sealed this
First Day of March, 2011

David J. Kappos
*Director of the United States Patent and Trademark Office*

SEQUENCE LISTING

<160> NUMBER OF SEQ ID NOS: 15

<210> SEQ ID NO 1
<211> LENGTH: 24
<212> TYPE: DNA
<213> ORGANISM: synthetic construct

<400> SEQUENCE: 1
caccaaccca aaccaaccca aacc                                          24

<210> SEQ ID NO 2
<211> LENGTH: 24
<212> TYPE: DNA
<213> ORGANISM: Synthetic construct

<400> SEQUENCE: 2
gaggaaaggg aagggaaagg aagg                                          24

<210> SEQ ID NO 3
<211> LENGTH: 40
<212> TYPE: DNA
<213> ORGANISM: Synthetic construct

<400> SEQUENCE: 3
caccaaccca aaccaaccca aaccggctca cgcctgtaat                         40

<210> SEQ ID NO 4
<211> LENGTH: 44
<212> TYPE: DNA
<213> ORGANISM: Synthetic construct

<400> SEQUENCE: 4
gaggaaaggg aagggaaagg aaggatccgc ctcccaggta gaat           44

<210> SEQ ID NO 5
<211> LENGTH: 44
<212> TYPE: DNA
<213> ORGANISM: Synthetic construct

<400> SEQUENCE: 5
gaggaaaggg aagggaaagg aaggatccgc ctcctgggtt caag           44

<210> SEQ ID NO 6
<211> LENGTH: 44
<212> TYPE: DNA
<213> ORGANISM: Synthetic construct

<400> SEQUENCE: 6
gaggaaaggg aagggaaagg aaggatccga tctgcctggt tctg           44

<210> SEQ ID NO 7
<211> LENGTH: 44
<212> TYPE: DNA
<213> ORGANISM: Synthetic construct

<400> SEQUENCE: 7
gaggaaaggg aagggaaagg aaggatccgt gagcgcaacg caat           44

<210> SEQ ID NO 8
<211> LENGTH: 823
<212> TYPE: DNA
<213> ORGANISM: Synthetic construct

<400> SEQUENCE: 8 gggcccccc tcgagaagcc gtgctgtcag catcagcatc atcggtgaga cctctcccca     60
agccctacag accctgggac tagggtgcag gacagcacag gctctaattt cctgccccat    120
tctggcctta tccctaacag ccaccccacc tctccctcca tgcacccaca cccaagcctc    180
ccctacccca cccaaattct gccaagagag cagccaagcc tctcccttct tccctctgag    240
ctaaaaaaag gaacagacgg ctgggcgcgg tggctcacgc ctgtaatccc aacactccat    300
gcatctggtg atgcgagctc gactctgggg aaaacactgg gttttcccag agtcgagcat    360
tctacctggg aggccagcta cttgagaggc tgaggcagga gaattgcttg aacccaggag    420
gcatagattg tgatgagcca agatcgcacc attgcatgcc agcctcggca acaaaagtga    480
aactccatct caaaaaaaaa agaaagggaa agactccact ggggctccca ctaaataacc    540
ctctctcaac ccgaagtctt cctttctgac tggatccaac tttgtcttcc agaaccaggc    600
agatccacta gttctagagc ggccgccacc gcggtggagc tccagctttt gttcccttta    660
gtgagggtta attccgagct ggcgtaatc atggtcatag ctgtttcctg tgtgaaattg    720
ttatccgctc acaattccac acaacatacg agccggaagc ataaagtgta aagcctgggg    780
tgcctaatga gtgagctaac tcacattaat tgcgttgcgc tca                      823

<210> SEQ ID NO 9
<211> LENGTH: 68
<212> TYPE: DNA
<213> ORGANISM: Synthetic construct

<400> SEQUENCE: 9

```
caccaaccca aaccaaccca aaccatgccg atgacctgca gaagccttcc tttcccttcc    60
cttttcctc                                                            68
```

<210> SEQ ID NO 10
<211> LENGTH: 68
<212> TYPE: DNA
<213> ORGANISM: Synthetic construct

<400> SEQUENCE: 10

```
caccaaccca aaccaaccca aaccgtactg caccaggcgg ccgcccttcc tttcccttcc    60
cttttcctc                                                            68
```

<210> SEQ ID NO 11
<211> LENGTH: 90
<212> TYPE: DNA
<213> ORGANISM: Synthetic construct

<400> SEQUENCE: 11

```
caccaaccca aaccaaccca aaccctggg gaggcatgcc gatgacctgc agaagccatg     60
ggatggcctt cctttccctt ccctttcctc                                     90
```

<210> SEQ ID NO 12
<211> LENGTH: 155
<212> TYPE: DNA
<213> ORGANISM: Synthetic construct

<400> SEQUENCE: 12

```
caccaaccca aaccaaccca aaccggctca cgcctgtaat cccaacactc catgcatctg    60
gtgatgcgag ctcgactctg gggaaaacac tgggttttcc cagagtcgag cattctacct   120
gggaggcgga tccttccttt ccttcccctt tcctc                              155
```

<210> SEQ ID NO 13
<211> LENGTH: 203
<212> TYPE: DNA
<213> ORGANISM: Synthetic construct

<400> SEQUENCE: 13

```
caccaaccca aaccaaccca aaccggctca cgcctgtaat cccaacactc catacgtctg    60
gtgatgcgag ctcgactctg gggaaaacac tgggttttcc cagagtcgag cattctacct   120
gggaggccag ctacttgaga ggctgaggca ggagaattgc ttgaacccag gaggcggatc   180
cttcctttcc cttcccttc ctc                                            203
```

<210> SEQ ID NO 14
<211> LENGTH: 386
<212> TYPE: DNA
<213> ORGANISM: Synthetic construct

<400> SEQUENCE: 14

```
caccaaccca aaccaaccca aaccggctca cgcctgtaat cccaacactc catgcatctg    60
gtgatgcgag ctcgactctg gggaaaacac tgggttttcc cagagtcgag cattctacct   120
gggaggccag ctacttgaga ggctgaggca ggagaattgc ttgaacccag gaggcataga   180
ttgtgatgag ccaagatcgc accattgcat gccagcctcg gcaacaaaag tgaaactcca   240
tctcaaaaaa aaaagaaagg gaaagactcc actggggctc cactaaaata accctctctc   300
aacccgaagt cttcctttct gactggatcc aactttgtct tccagaacca ggcagatcgg   360
atccttcctt tccttccct ttcctc                                         386
```

-continued

```
<210> SEQ ID NO 15
<211> LENGTH: 605
<212> TYPE: DNA
<213> ORGANISM: Synthetic construct

<400> SEQUENCE: 15
caccaaccca aaccaaccca aaccggctca cgcctgtaat cccaacactc catacgtctg      60
gtgatgcgag ctcgactctg gggaaaacac tgggttttcc cagagtcgag cattctacct     120
gggaggccag ctacttgaga ggctgaggca ggagaattgc ttgaacccag gaggcataga     180
ttgtgatgag ccaagatcgc accattgcat gccagcctcg gcaacaaaag tgaaactcca     240
tctcaaaaaa aaaagaaagg gaaagactcc actggggctc ccactaaata accctctctc     300
aacccgaagt cttcctttct gactggatcc aactttgtct tccagaacca ggcagatcca     360
ctagttctag agcggccgcc accgcggtgg agctccagct tttgttccct ttagtgaggg     420
ttaattccga gcttggcgta atcatggtca tagctgtttc ctgtgtgaaa ttgttatccg     480
ctcacaattc cacacaacat acgagccgga agcataaagt gtaaagcctg gggtgcctaa     540
tgagtgagct aactcacatt aattgcgttg cgctcacgga tccttccttt cccttccctt     600
tcctc                                                                 605
```